(12) United States Patent
Contente et al.

(10) Patent No.: US 6,796,973 B1
(45) Date of Patent: Sep. 28, 2004

(54) VAGINAL DISCHARGE COLLECTION DEVICE AND INTRAVAGINAL DRUG DELIVERY SYSTEM

(75) Inventors: Audrey Contente, New York, NY (US); Bruce F. Ross, Yorba Linda, CA (US); Richard C. Potter, Seeley Lake, MT (US)

(73) Assignee: Instead, Inc., La Jolla, CA (US)

( * ) Notice: Subject to any disclaimer, the term of this patent is extended or adjusted under 35 U.S.C. 154(b) by 1826 days.

(21) Appl. No.: 08/215,062

(22) Filed: Mar. 21, 1994

Related U.S. Application Data

(62) Division of application No. 07/904,367, filed on Jun. 26, 1992, now Pat. No. 5,295,984, and a continuation-in-part of application No. 07/852,265, filed on Jun. 8, 1992, now abandoned, and a continuation-in-part of application No. 07/865,746, filed on Apr. 10, 1992, now abandoned, which is a continuation-in-part of application No. 07/817,498, filed on Jan. 7, 1992, now abandoned, which is a division of application No. 07/446,553, filed on Dec. 7, 1989, now abandoned.

(51) Int. Cl.$^7$ .................................................. A61F 5/44
(52) U.S. Cl. ........................ 604/354; 604/330; 128/832
(58) Field of Search ................... 604/358, 890.1–892.1, 604/317–357, 403–416; 128/760, 767, 769, 830–841, 844, 883–887

(56) References Cited

U.S. PATENT DOCUMENTS

| | | | |
|---|---|---|---|
| 71,414 A | 11/1867 | Rohleder | |
| 1,083,721 A | 1/1914 | Asch | |
| 1,891,761 A | * 12/1932 | Goddard | ..................... 128/887 |
| 1,986,504 A | 1/1935 | Cubbon | |
| 1,996,242 A | 4/1935 | Hagedorm | |
| 2,024,539 A | 12/1935 | Schmid | |
| 2,061,384 A | 11/1936 | Menegold | |
| 2,071,248 A | 2/1937 | Cambell | |
| 2,079,022 A | 5/1937 | Martin | |
| 2,103,319 A | 12/1937 | Clark, Jr. | |
| 2,141,040 A | * 12/1938 | Holt | ........................... 128/887 |
| 2,234,494 A | 3/1941 | Lay | |
| 2,324,656 A | 7/1943 | Vincent | |
| 2,443,943 A | 6/1948 | Young | |
| 2,529,363 A | 11/1950 | Ballard et al. | |
| 2,534,900 A | 12/1950 | Chalmers | |
| 2,616,426 A | * 11/1952 | Gordon | ...................... 128/887 |
| 2,697,057 A | 12/1954 | Senger et al. | |

(List continued on next page.)

FOREIGN PATENT DOCUMENTS

| | | |
|---|---|---|
| AU | 5471/31 | 1/1933 |
| AU | 15818/70 | 12/1971 |
| CA | 677336 | 1/1964 |
| DE | 205896 | 1/1909 |
| DE | 256410 | 2/1913 |
| DE | 444367 | 5/1927 |

(List continued on next page.)

OTHER PUBLICATIONS

Durex Products Inc., "Durex Notes," No. 11, Dec. 7, 1949.

Primary Examiner—Glenn K. Dawson
(74) Attorney, Agent, or Firm—Dickstein Shapiro Morin & Oshinsky LLP

(57) ABSTRACT

A vaginal discharge collection device is formed of an elastomeric rim and a flexible film reservoir. The rim may have a generally rectangular cross section and forms a collection space for collecting vaginal discharge. The reservoir may be collapsible so as to be substantially enclosed within the rim when the device is being used. Advantageously, the rim and the reservoir are arranged such that compressing diametrically opposed portions of the rim toward each other causes a leading portion of the rim to dip downwardly to facilitate insertion of the device. The device is ergonomically constructed so as to be convenient to use, comfortable to wear internally, and reliable. A system for reliably, comfortably and conveniently introducing agents, including drugs and other substances, into the vaginal canal is also disclosed.

26 Claims, 7 Drawing Sheets

U.S. PATENT DOCUMENTS

| | | | |
|---|---|---|---|
| 2,915,065 | A | 12/1959 | Lyons et al. |
| 3,036,570 | A | 5/1962 | Milgrom et al. |
| 3,037,508 | A | 6/1962 | Friedman |
| 3,042,029 | A | 7/1962 | Johansson |
| 3,060,931 | A | 10/1962 | Clark |
| 3,128,767 | A | 4/1964 | Nolan |
| 3,169,522 | A | 2/1965 | Monett |
| 3,216,422 | A | 11/1965 | Steiger et al. |
| 3,404,682 | A | 10/1968 | Waldron |
| 3,626,942 | A | 12/1971 | Waldron |
| 3,841,333 | A | 10/1974 | Zalucki |
| 3,845,766 | A | 11/1974 | Zöller |
| 3,854,480 | A | 12/1974 | Zaffaroni |
| 3,983,874 | A * | 10/1976 | Davis et al. ................. 604/330 |
| 4,012,496 | A | 3/1977 | Schöpflin et al. |
| 4,031,886 | A | 6/1977 | Morhenn |
| 4,093,490 | A * | 6/1978 | Ziets et al. ................. 128/837 |
| 4,198,965 | A | 4/1980 | Strickman et al. |
| 4,198,976 | A | 4/1980 | Drobish et al. |
| 4,200,090 | A | 4/1980 | Drobish |
| 4,219,016 | A | 8/1980 | Drobish et al. |
| 4,232,673 | A | 11/1980 | Bucalo |
| 4,261,352 | A | 4/1981 | Sedlacek |
| 4,286,593 | A | 9/1981 | Place et al. |
| 4,300,544 | A | 11/1981 | Rudel |
| 4,311,543 | A | 1/1982 | Strickman et al. |
| 4,320,751 | A * | 3/1982 | Loeb ........................ 604/331 |
| 4,326,510 | A | 4/1982 | Buckles |
| 4,332,243 | A | 6/1982 | Gutnick |
| 4,369,219 | A | 1/1983 | Goepp |
| 4,381,771 | A | 5/1983 | Gabbay |
| 4,427,477 | A | 1/1984 | Milgrom |
| 4,526,578 | A | 7/1985 | Wong |
| 4,553,972 | A | 11/1985 | Vickery |
| 4,589,880 | A * | 5/1986 | Dunn et al. ................. 128/832 |
| 4,607,630 | A | 8/1986 | Spits |
| 4,630,602 | A | 12/1986 | Strickman et al. |
| 4,640,272 | A | 2/1987 | Monett |
| 4,711,235 | A | 12/1987 | Willis |
| 4,770,167 | A * | 9/1988 | Kaali et al. ................. 128/788 |
| 4,785,805 | A | 11/1988 | Joffe et al. |
| 4,822,616 | A | 4/1989 | Zimmermann et al. |
| 4,848,363 | A | 7/1989 | Cattanach |
| 4,858,624 | A | 8/1989 | Shihata |
| 4,883,071 | A | 11/1989 | Pickhard et al. |
| 4,895,170 | A | 1/1990 | Tlapek et al. |
| 4,923,440 | A | 5/1990 | Genaro |
| 4,955,875 | A * | 9/1990 | Knowles ..................... 604/331 |
| 4,959,216 | A | 9/1990 | Daunter |
| 4,961,436 | A | 10/1990 | Koch |
| 4,989,618 | A | 2/1991 | Shihata |
| 5,002,540 | A | 3/1991 | Brodman et al. |
| 5,044,376 | A | 9/1991 | Shields |
| 5,207,232 | A | 5/1993 | Shihata |
| 5,228,456 | A | 7/1993 | Karg et al. |
| 5,231,992 | A | 8/1993 | Leon |
| 5,295,984 | A | 3/1994 | Contente et al. |
| 5,398,698 | A | 3/1995 | Hiller et al. |
| 6,264,638 | B1 * | 7/2001 | Contente ..................... 604/285 |

FOREIGN PATENT DOCUMENTS

| | | |
|---|---|---|
| DE | 553547 | 9/1930 |
| DE | 589399 | 12/1933 |
| DE | 6250530 | 10/1935 |
| DE | 845832 | 8/1952 |
| EP | 134671 | 11/1978 |
| EP | 0009518 A1 | 4/1980 |
| EP | 129271 | 12/1984 |
| EP | 247837 | 12/1987 |
| EP | 0647144 B1 | 3/2002 |
| FR | 2388545 | 3/1985 |
| GB | 21588 | 8/1897 |
| GB | 260600 | 10/1926 |
| WO | WO 87/01581 | 3/1987 |
| WO | 8900415 | 1/1989 |
| WO | WO 91/08779 | 6/1991 |
| WO | WO 94/00168 | 1/1994 |

* cited by examiner

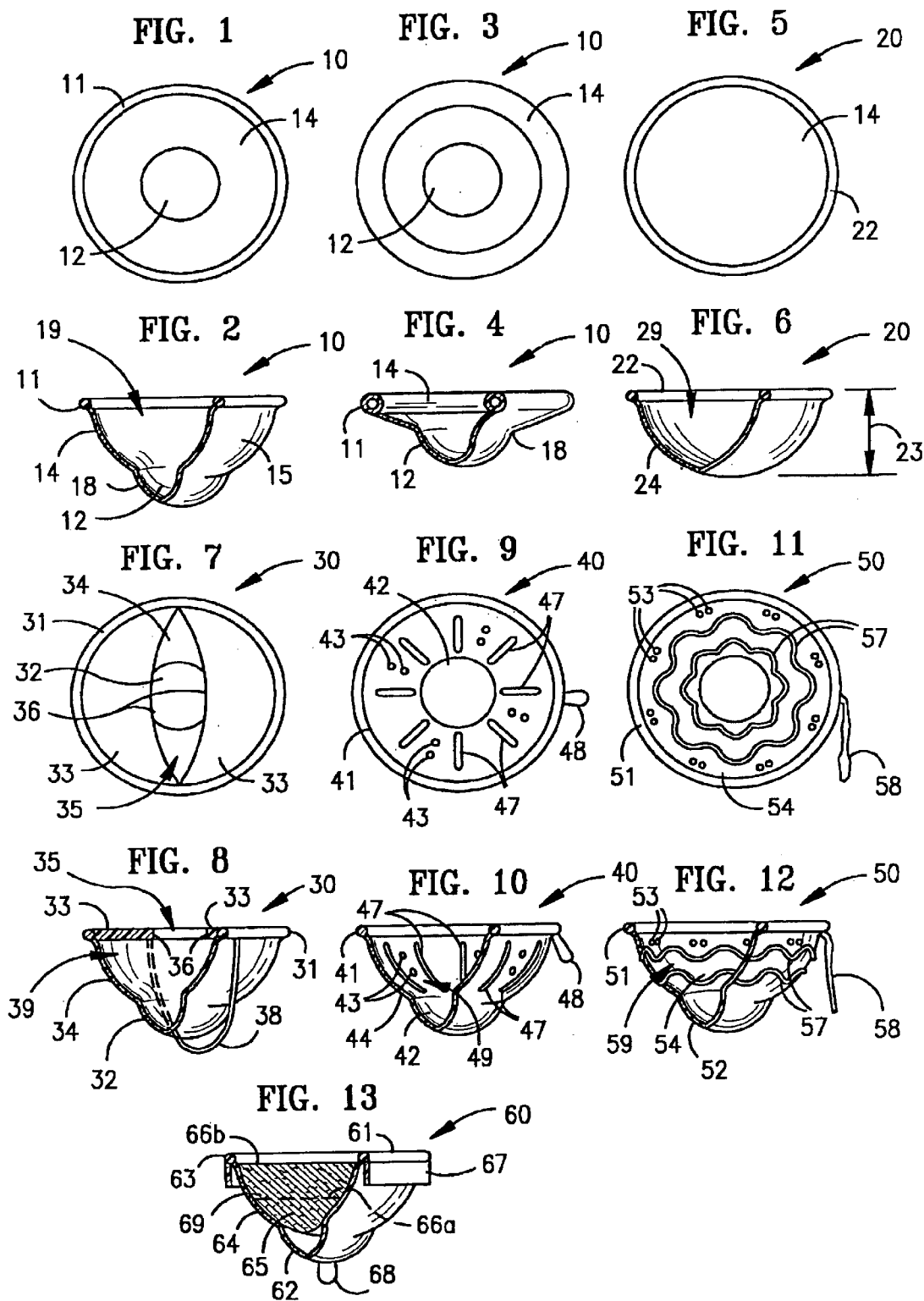

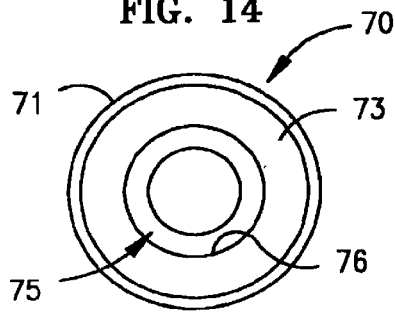
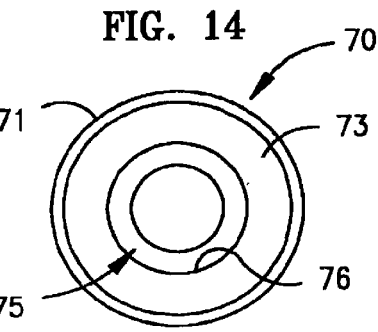
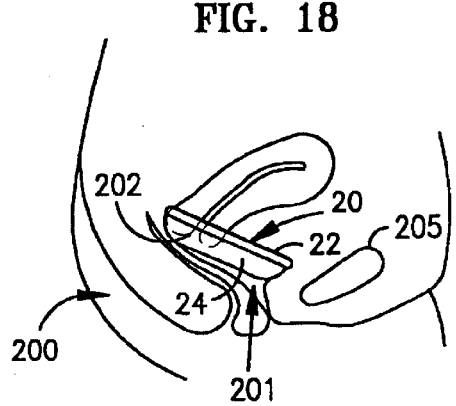
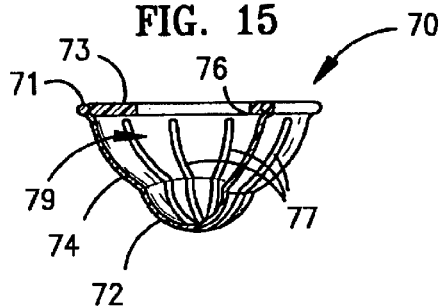
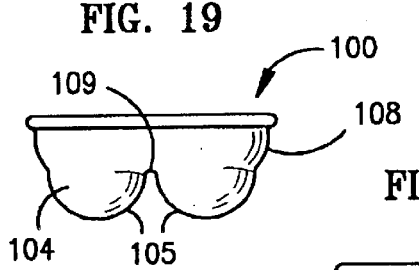
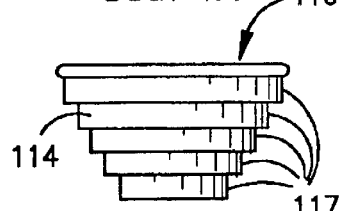
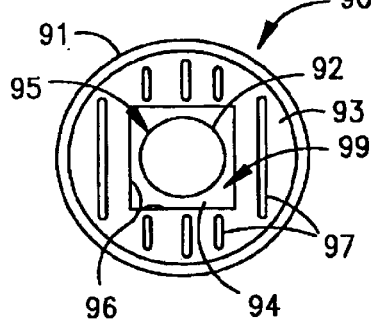
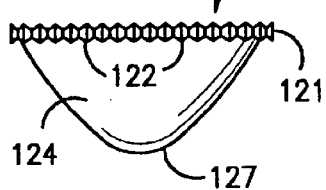
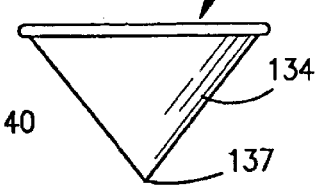
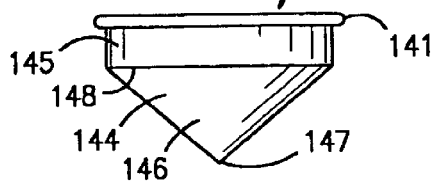

VAGINAL DISCHARGE COLLECTION DEVICE AND INTRAVAGINAL DRUG DELIVERY SYSTEM

This is a divisional of U.S. patent application Ser. No. 07/904,367, filed Jun. 26, 1992, which is a continuation-in-part of U.S. patent application Ser. No. 07/817,498, filed Jan. 7, 1992, now abandoned, which is a divisional of U.S. patent application Ser. No. 07/446,553, filed Dec. 7, 1989, now abandoned, the entire disclosure of which is incorporated herein by reference. U.S. Ser. No. 08/215,062 is also a continuation-in-part of U.S. patent application Ser. No. 07/865,746, filed Apr. 10, 1992, now abandoned, which is a continuation of U.S. patent application Ser. No. 07/446,553, filed Dec. 7, 1989, now abandoned. This is also a continuation-in-part of U.S. patent application Ser. No. 07/852,265, filed Jun. 8, 1992 (based on International Patent Application Number PCT/US90/07159, filed Dec. 7, 1990), now abandoned, the entire disclosure of which is incorporated herein by reference.

BACKGROUND OF THE INVENTION

The present invention relates generally to feminine hygiene devices, and more particularly to a vaginal discharge collection device for collecting vaginal discharge. The present invention also relates generally to the intravaginal delivery of drugs and other substances.

From the time after World War I, when bandages were marketed as sanitary napkins, to the present, there have been essentially only two types of commercially available menstrual collection products: sanitary napkins and tampons. Sanitary napkins, including the newer pads and shields, have the disadvantages of bulk, odor and leakage. They also present disposal problems, and they are sometimes detectable to others. Their absorbent nature can also create problems of contamination and infection. Tampons are also disadvantageous. The basic design of the tampon does not stop leakage and the externally worn string can lead to contamination. Tampons have fibers which irritate the vaginal mucosa. Absorptive tampons can also contribute to serious infections.

U.S. Pat. No. 3,983,874 (Davis), U.S. Pat. No. 3,128,767 (Nolan), and U.S. Pat. No. 3,216,422 (Steiger) disclose absorptive cup-shaped vaginal tampons. These devices are bulky and would be difficult to use and uncomfortable to wear, and would have the same dangers of infection presented by conventional absorptive tampons. Other internal vaginal discharge collection devices are disclosed in U.S. Pat. No. 3,845,766 (Zoller), U.S. Pat. No. 3,841,333 (Zalucki), U.S. Pat. No. 3,626,942 (Waldron), U.S. Pat. No. 3,404,682 (Waldron), U.S. Pat. No. 2,616,426 (Gordon), U.S. Pat. No. 2,534,900 (Chalmers), U.S. Pat. No. 1,986,504 (Cubbon), and U.S. Pat. No. 71,414 (Rohleder). These devices all suffer from poor ergonomic design. They would be difficult to insert and remove, uncomfortable to wear, and/or unreliable.

The Waldron and Chalmers devices are worn in a lower region of the vaginal canal and generate suction, particularly during removal. These devices would cause irritation and pressure, and would damage the delicate vaginal tissue. The suction generated by the devices would also make the devices difficult to remove, and would tend to cause spillage.

Further, the Davis, Nolar, Gordon and Rohleder devices have rims with springs embedded therein. Such springs make the devices unnecessarily complicated and expensive to manufacture. The Zoller, Zalucki, Waldron and Chalmers devices have complicated configurations that would be relatively expensive to manufacture. The exterior configurations of these devices may also cause irritation when worn internally. The Cubbon device has a small flat loop vulcanized to the under edge of a rubber ring. Providing this loop complicates the device unnecessarily. The loop may also cause irritation during use. With or without the loop, the Cubbon device suffers from poor ergonomic design.

Accordingly, there is a need in the art for a vaginal discharge collection device that avoids the problems associated with napkins and tampons, and that is convenient, comfortable, reliable and economical.

Prior art systems for delivering drugs and other substances into the vaginal canal are disclosed by U.S. Pat. No. 4,895,170 (Tlapek), U.S. Pat. No. 4,589,880 (Dunn), U.S. Pat. No. 4,526,578 (Wong), U.S. Pat. No. 4,311,543 (Strickman), U.S. Pat. No. 4,286,587 (Wong), U.S. Pat. No. 4,219,016 (Drobish), U.S. Pat. No. 4,200,090 (Drobish), U.S. Pat. No. 4,198,976 (Drobish), and U.S. Pat. No. 4,198,965 (Strickman), and British Patents Nos. 260,600 (Fiessler) and 21,588 (Fickert). These devices are structurally unsatisfactory. For example, the Tlapek device has a semi-circular loop used for removal. This loop unnecessarily complicates the Tlapek device and may cause irritation during use. The Wong ('587) device has a circular cross section. As a result, this device would tend to twist upon compression, making insertion of the device difficult. All of the prior art systems would be difficult to insert and remove, uncomfortable to wear, unreliable, and/or uneconomical to manufacture and market.

Accordingly, there is a need in the art for an intravaginal substance delivery system that can be conveniently and reliably used, and that can be used without discomfort, particularly during menses.

SUMMARY OF THE INVENTION

The present invention alleviates to a great extent the disadvantages of the known vaginal discharge collection devices by providing a vaginal discharge collection device including an elastomeric rim with a generally rectangular cross section which creates a collection space for collecting vaginal discharge, and a flexible film reservoir attached to the rim.

In one aspect of the invention, the reservoir is collapsible so as to be substantially enclosed within the rim when the device is located within the vaginal canal.

In another, separate aspect of the invention, the rim and the reservoir of a vaginal discharge collection device are arranged such that compressing diametrically opposed portions of the rim toward each other causes a leading portion of the rim to dip downwardly to facilitate proper insertion of the device under the cervix.

In another aspect of the present invention, the dimensions and materials of the device, including the dimensions and materials of the rim, are selected so as to optimize the device's convenience, comfort and reliability.

In another aspect of the invention, the collector includes a closure structure for at least partially covering the opening for inhibiting the exit of vaginal discharge from the collection space. One embodiment of the closure structure includes a membrane extending over the area within the rim. The membrane is slit or divided into two approximately equal parts approximately along a line extending across the diameter of the rim and approximately through the radial center of the rim. The two parts of the membrane may each have an area larger than half of the circular area defined by the rim so as to overlap along the slit and/or extend loosely and not be stretched tightly across the area defined by the rim. This loose and/or overlapping structure is to allow collection of fluid into the device through the slit but to inhibit exit of the fluid from the device. Forces on the device during removal will tend to close together the overlapping parts of the slit membrane to prevent the exit of fluid.

Because a substantially looser fit is needed to inhibit the passage of menstrual fluid than to inhibit the passage of sperm, the structure of the present invention may be smaller than the contraceptive diaphragm type devices to increase comfort during wearing while still being held in position by compression of the vaginal wall on the rim. The comfort is achieved by a rim that will conform to the individual and that will be more flexible and less rigid than that of the diaphragm type devices. Thus, a single size of the collector according to the present invention will be adequate for use for a range of sizes of vaginal canals, unlike the diaphragm type devices which must be individually fit by a medical doctor or specially trained nurse and which are available only by prescription. Moreover, the diaphragm type devices must last for long periods of time and must be constructed of heavyweight materials. Therefore, the invention may be less expensive than the diaphragm type devices and may be disposable.

Another advantage of the present invention is that, because it may be made of an elastomeric material that is chemically inert and non-toxic, the present invention should not be prone to health problems that the current products seem to cause. Moreover, this soft material will allow for adjustment to individual shapes and afford excellent comfort while maintaining its original form. The present invention seals off the blood environment to inhibit the growth of bacteria and entry of air and thus hinders the odor which results from the oxidation and decomposition of the menstrual flow.

In another aspect of the invention, the collector may effect intravaginal drug delivery of time release and non-time release medicants for all diseases of the vagina and other reproductive organs and any and all diseases of the entire female anatomy wherein vaginal absorption can be utilized for both menstruating and non-menstruating females. For example, for the treatment of yeast and fungal infection, medication can be delivered without interruption due to menstruation.

Moreover, for providing a safe sex barrier the device may be used as a barrier during sexual contact to aid in the prevention of the transmission of diseases. The effectiveness of the device in this regard may be enhanced by using the device with, or for the delivery of, non-oxynol 9 or other specific medicants.

Additionally, the invention may be used for intravaginal delivery of hormones for birth control and for treatment of the female anatomy, such as during menopause.

The invention may also be used for the delivery of time released and non-time released deodorizing materials for odor prevention, for the delivery of lubrication and for the delivery of steroids, anti-bacterial agents or any pharmacological agent, chemical, natural, or homeopathic agents.

Moreover, the invention may be used for intravaginal delivery of anesthetic for local surgical procedures and for general surgical procedures and for the delivery of pain relieving medication for intermittent and chronic pain, as well as for drug delivery for pregnant women for any and all prophylaxis and illnesses particular to the fetus and/or mother-to-be.

The invention may be used for the delivery of drugs and other substances in veterinary applications including primates other than humans and other animals.

Moreover, the invention may be employed as an aid to conception for humans, primates, and other animals. Conception can be aided by either using the collector for retaining sperm in the vaginal vault after intercourse or by placing sperm in or on the collector and then inserting it in the vaginal vault. This is different from and not a substitute for the medical procedures of artificial insemination that are required for certain circumstances and that are done by doctors in a clinical/hospital setting.

The invention may also be used as a specimen collector to collect blood and/or vaginal, cervical and/or uterine discharge.

The present invention also relates to a method of using a vaginal discharge collection device, wherein the device is held in place by a resilient outward holding force.

The present invention also relates to an improved system for reliably, comfortably and conveniently introducing drugs and other substances into the vaginal canal.

It is an object of the present invention to provide a vaginal discharge collection device that is convenient to use, comfortable to wear, and reliable.

Another object of the invention is to provide an ergonomically improved system for the intravaginal delivery of drugs or other substances.

Another object of the invention is to provide a device for vaginal discharge collection and/or intravaginal substance delivery, with the device being designed for economical mass production, such that the device can be conveniently disposed of after a single use.

Another object of the invention is to provide a vaginal discharge collection device that can be used to collect menstrual discharge during sexual intercourse.

An object of the present invention is to provide a vaginal discharge collector.

It is another object of the present invention to provide a vaginal discharge collector which has an adjustable discharge collection capacity.

It is yet another object of the present invention to provide a vaginal discharge collector with the foregoing advantages and which may be adjusted to a number of intermediate positions between and including a rolled-up position and a rolled-down position.

It is a further object of the present invention to provide a vaginal discharge collector with any of the foregoing advantages and which provides a reservoir which has essentially constant capacity in either the rolled-up and rolled-down positions.

It is another object of the present invention to provide a vaginal discharge collector with any of the foregoing advantages and which provides an absorbent material for absorbing and holding collected liquid.

It is still another object of the present invention to provide a vaginal discharge collector with any of the foregoing advantages and which provides a closure structure for inhibiting the exit of collected discharge fluid.

It is yet a further object of the present invention to provide a vaginal discharge collector with any of the foregoing advantages and which provides time released and non-timed released dosages of substances for both menstruating and non-menstruating females so that there will be substantially no interruption of treatment, which substance may be, for example, medication, lubrication, deodorants, hormones and analgesics.

It is another object of the present invention to provide a vaginal discharge collector with any of the foregoing advantages and which does not require individual fitting for each user and which may be produced economically enough to be used as a disposable product.

It is yet another object of the present invention to provide a vaginal discharge collector with any of the foregoing advantages and which is easy to insert and remove without scraping delicate tissue.

It is still another object of the present invention to provide a vaginal discharge collector with any of the foregoing advantages and which provides a barrier against the blood environment.

It is a further object of the present invention to provide a vaginal discharge collector with any of the foregoing advantages and which is light weight without the bulk associated with other devices and which once inserted cannot be felt by the user so that the user is free of the annoying awareness associated with other devices.

It is yet a further object of the present invention to provide a vaginal discharge collector with any of the foregoing advantages and which during use is undetectable by others.

It is still a further object of the present invention to provide a vaginal discharge collector with any of the foregoing advantages and which is designed to meet the need for a feminine hygiene product that is neither an internal absorbent tampon nor an external absorbent pad.

It is another object of the present invention to provide a vaginal discharge collector with any of the foregoing advantages and which is inexpensive and therefore available to all women.

Other objects and advantages of the present invention will become apparent from the following detailed description and drawings which illustrate preferred embodiments of the present invention.

BRIEF DESCRIPTION OF THE DRAWINGS

FIG. 1 is a top view of a first preferred embodiment of a vaginal discharge collector according to the present invention in a rolled-down position.

FIG. 2 is a partial cut-away side view of the collector of FIG. 1.

FIG. 3 is a top view of the collector of FIG. 1 in a rolled-up position.

FIG. 4 is a partial cut-away side view of the collector of FIG. 3.

FIG. 5 is a top view of a second preferred embodiment of a vaginal discharge collector according to the present invention.

FIG. 6 is a partial cut-away side view of the collector of FIG. 5.

FIG. 7 is a top view of a third preferred embodiment of a vaginal discharge collector according to the present invention.

FIG. 8 is a partial cut-away side view of the collector of FIG. 7.

FIG. 9 is a top view of a fourth preferred embodiment of a vaginal discharge collector according to the present invention.

FIG. 10 is a partial cut-away side view of the collector of FIG. 9.

FIG. 11 is a top view of a fifth preferred embodiment of a vaginal discharge collector according to the present invention.

FIG. 12 is a partial cut-away side view of the collector of FIG. 11.

FIG. 13 is a top view of a sixth preferred embodiment of a vaginal discharge collector according to the present invention.

FIG. 14 is a top view of a seventh preferred embodiment of a vaginal discharge collector according to the present invention.

FIG. 15 is a partial cut-away side view of the collector of FIG. 14.

FIG. 16 is a top view of an eighth preferred embodiment of a vaginal discharge collector according to the present invention.

FIG. 17 is a top view of a ninth preferred embodiment of a vaginal discharge collector according to the present invention.

FIG. 18 is a view of the collector of FIG. 5 in place in the vaginal canal.

FIG. 19 is a side view of a tenth preferred embodiment of a vaginal discharge collector according to the present invention.

FIG. 20 is a side view of an eleventh preferred embodiment of a vaginal discharge collector according to the present invention.

FIG. 21 is a side view of a twelfth preferred embodiment of a vaginal discharge collector according to the present invention.

FIG. 22 is a side view of a thirteenth preferred embodiment of a vaginal discharge collector according to the present invention.

FIG. 23 is a side view of a fourteenth preferred embodiment of a vaginal discharge collector according to the present invention.

DETAILED DESCRIPTION OF PREFERRED EMBODIMENTS

Figure 24:
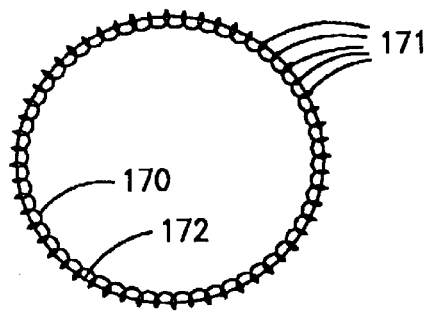
FIG. 24 is a schematic view of the rim structure of the collector of FIG. 7.

Refer now to FIGS. 1–4, there being shown a first preferred embodiment of a vaginal discharge collector, generally designated by reference numeral 10, according to the present invention. The collector 10 includes a resilient circular rim 11. The body 14 of the collector 10 includes a cup-shaped membrane wall 15 extending downward from the rim and terminating in a reservoir 12 to form a collection space 19. The membrane wall 15 includes at its bottom a reservoir 12 that is a bubble-like protrusion extending at edge 18 from the body 14 surface defined by the membrane wall 15. As shown in FIGS. 1 and 2, the collector 10 is in a rolled-down position. As shown in FIGS. 3 and 4 the collector 10 is in a rolled-up position with the body membrane 14 rolled around the rim 11. In the rolled-up position the collection space 19 has a smaller volume than it has in the rolled-down position.

In adjusting the collector 10 from the rolled-down position of FIGS. 1 and 2 to the rolled-up position of FIGS. 3 and 4, the body 14 is rolled onto the rim 11. Additionally, the body 14 may be rolled onto the rim 11 to a number of intermediate positions between the rolled-down position and the rolled-up position. Because the inside of the rim 11 has a smaller diameter than the outside of the rim 11, as the rim 11 is twisted inside out to roll around itself, the inner portion of the rim 11 is stretched. Because the rim 11 is made from a resilient material, it will tend to relax to a position where its inside is facing inwardly and its outside is facing outwardly so that the rim is in a low state of compression and extension. In other positions, such as with the inside of the rim 11 facing outward, the inside of the rim would be stretched and the outside would be in compression. Therefore, during rolling of the body 14 onto or off of the rim 11, the rim 11 tends to rest in a number of discreet intermediate positions. The number of such positions will depend upon the depth of the body 14, the thickness of the body 14 and the tightness upon which the body 14 is wound around the rim 11.

The capacity of the reservoir 12 is essentially the same in either the rolled-down or rolled-up position. In the rolled-up position as shown in FIGS. 3 and 4, the reservoir 12 has a capacity that is essentially the same as in the rolled-down position of FIGS. 1 and 2. The capacity of the reservoir 12 remains essentially unchanged from the rolled-down through the intermediate positions to the rolled-up position because it is essentially a bubble-like protrusion extending off of the surface of the body 14. The upper extent of the reservoir 12 is defined by the edge 18 where the reservoir 12 begins to extend from the body 14. When the collector 10 is in the rolled-up position of FIGS. 3 and 4 and the body 14 extends nearly flatly over the area within the ring shaped rim 11, the reservoir 12 still extends outward off of the surface of the body 14. Even though the edge 18 of the reservoir 12 may stretch or expand to some extent, relative to the change in the capacity of the total collector space 19, the capacity of the reservoir remains essentially constant. Thus, essentially constant for purposes of the invention means relatively less change than the change in the total collection space.

The collector 10 is composed of a latex rubber and may be formed by a latex dipping process in which a mandrel is dipped into a tank of coagulating agent, and then dipped into a tank of liquid rubber latex which coagulates on the mandrel. It is then subjected to drying and curing with heat and the device is removed from the mandrel. The material of the preferred embodiment is elastomeric, such as a latex rubber and similar materials. Further information regarding the latex dipping process may be obtained from Faultess Rubber Company, Ashland, Ohio. Materials for the collector may be chosen which may be impregnated with a substance to be delivered during use of the device. Such materials are generally known, such as described in U.S. Pat. No. 4,589,880. Other suitable methods of making the collector may be used, such as by molding.

The rim 11 of the collector 10 is formed entirely of solid latex rubber. However, as discussed below with reference to other preferred embodiments, alternative rim constructions may be used. The diameter of the rim is preferably about two to about four inches (about five to about ten centimeters). The thickness of the rim is preferably less than about one quarter inch (about six millimeters) to result in the greatest degree of comfort to the user. The thickness of the wall, which is substantially impervious to liquid, of the body 14 and the reservoir 12 is preferably more than about one ten thousandth of an inch (about two micrometers). In a rolled-down position, the depth of the collector 10 from the rim 11 to the bottom of the reservoir 12 is preferably about one to three inches (about two to eight centimeters). The depth of the reservoir 12 from the edge 18 to the bottom of the reservoir 12 is preferably about one sixteenth to one half of an inch (about two millimeters to about thirteen millimeters). The volume of the collection space 19 is preferably about one to about two ounces (about fifteen to about thirty milliliters). The thickness and diameter of the rim will depend upon the stiffness of the material used as the rim should be resilient and flexible to be inserted into position and to exert sufficient force to hold the collector 10 in position during use as discussed further below in reference to FIG. 18. The thickness of the body 14 will depend upon the properties of the material used so that the body 14 will have sufficient strength and flexibility.

Refer to FIGS. 5 and 6, there being shown a second preferred embodiment of a vaginal discharge collector, generally designated by reference numeral 20, according to the present invention. The collector 20 includes a resilient circular rim 22. The body 24 of the collector 20 is an impervious cup-shaped membrane wall extending downward from the rim 22 to form a collection space 29. As shown in FIGS. 5 and 6 the collector 20 is in a rolled-down position. Like the collector 10, the collector 20 may be positioned in a rolled-up position with the body membrane 24 rolled around the rim 22. In the rolled-up position the space 29 has a smaller volume than it has in the rolled-down position. The construction of the collector 20 is essentially the same as the collector 10, but the collector 20 does not include the reservoir feature.

The purpose of the device 20 is to collect vaginal discharge, including uterine, cervical and mucosal discharge, particularly blood and tissue sloughed off from a woman's uterus during menstruation.

In operation, the device 20 is inserted into the woman's vaginal canal 201 (FIG. 18) such that portions of the rim 22 are located behind the cervix 202 and behind the pubic bone 205. In this position, the resilient rim 22 exerts a resilient, radially outward force on the wall of the vaginal canal 201. The rim 22 also contacts and exerts a force against the wall of the vaginal canal 201 at points around the periphery of the rim 22, which force is sufficient to effectively prevent menses or other vaginal discharge from passing between the rim 22 and the vaginal canal wall 201. The resilient outward force of the rim 22 is sufficient to maintain the device 20 in its illustrated position.

In FIG. 18, collector 20 is shown rolled to an intermediate position between the rolled-up and rolled-down positions.

Also note that collector 20 is rolled so that the wall 24 extends downward from the inside of rim 22. Conversely, as shown in FIG. 4, wall 14 of collector 10 is rolled in an alternative manner such that the wall 14 extends down from the outside of rim 11.

The outward force of the resilient rim 22 is also sufficient to effectively prevent vaginal discharge from passing between the rim 22 and the wall of the vaginal canal 201. Therefore, discharge from the cervix 202 is collected within the cup-shaped body 24. After a period of time, the device 20 is removed from the vaginal canal 201, and disposed of along with the collected vaginal discharge. A new device 20 is then inserted into the position illustrated in FIG. 18.

The amount of discharge that can be collected within the body 24 is a function of the device's depth 23 (FIG. 6). Increasing the depth 23 increases the amount of discharge that can be collected within the device 20, and therefore increases the amount of time that the device 20 can be used. An increased depth 23 also makes it easy to remove the device 20, as explained in more detail below. However, the depth 23 cannot be so great as to cause discomfort or make it difficult to insert the device 20 into the vaginal canal 201. Generally, the depth 23 of the device 20 measured from the top of the rim 22 to the bottom of the body 24 is at least about one and one-half centimeters and no more than about eight centimeters. A preferred range for the depth 23 is about four to about six centimeters.

The cross sectional thickness of the round rim 22 will depend upon the stiffness of the material used. The rim 22 should be flexible enough to be easily and reliably inserted into position, and yet stiff enough to exert sufficient radially outward force to hold the device 20 in position and to adequately prevent discharge from leaking around the rim 22, i.e., between the rim 22 and the wall of the vaginal canal 201. In the illustrated embodiment, the round rim 22 is formed entirely of an appropriately stiff elastomer, with a thickness of about six millimeters.

The wall of the cup-shaped body 24 should be thick enough to provide the desired strength, flexibility, durability and fluid imperviousness. In the illustrated embodiment, the body 24 is formed of latex rubber and is about two mils thick.

The device 20 may be formed by a latex dipping process involving the following steps: dipping a mandrel into a tank of coagulating agent; then dipping the mandrel into a tank of liquid rubber latex which coagulates on the mandrel; drying and curing the coagulated rubber latex; and removing the cured device from the mandrel. Other suitable methods of making the device 20, such as molding, may be used.

FIGS. 7 and 8 show a third preferred embodiment of a vaginal discharge collector, generally designated by reference numeral 30, according to the present invention. The collector 30 includes a resilient circular rim 31. The body 34 of the collector 30 is a cup-shaped membrane wall extending downward from the rim to form a collection space 39. The membrane wall includes at its bottom a reservoir 32 that is a bubble-like protrusion on the body 34 surface defined by the membrane. As shown in FIGS. 7 and 8, the collector 30 is in a rolled-down position. Similar to the collector 10 as shown in FIGS. 3 and 4, the collector 30 may be positioned in a rolled-up position with the body membrane 34 rolled around the rim 31. In the rolled-up position the space 39 has a smaller volume than it has in the rolled-down position. The collector 30 includes a closure means in the form of two membranes 33 to inhibit menses or other vaginal discharge from exiting the collection space 39. Membrane 33 extends across the circular area defined by the rim 31 forming, between their edges 36, a slit 35 which extends across the diameter of the rim 31. The edges 36 are curved so that the width of slit 35 is greatest at the center and the edges 36 come together at the rim 31. The area of the slit 35 is preferably between about five percent and about ninety five percent of the area defined by the rim 31. The sizes of the slit 35 and the membrane 33 are chosen such that the slit 35 is large enough for fluid to enter the collector 30 and the membranes 33 inhibit the exit of fluid to the desired extent. The thickness of the membranes 33 is preferably greater that about one ten thousandth of an inch (about two micrometers). If the membranes are used for drug delivery, the size and thickness of the membrane may be chosen to meet the dosage needs. The collector 30 also includes a removal means in the form of a looped string 38 which is attached to opposite points on the rim 31 and is long enough to be grasped by the user for removal of the collector 30 from its use position in the vaginal canal. The structure of the rim 31 of the collector 30 includes a coil spring extending within the elastomeric covering material. The structure of rim 31 is discussed in more detail with reference to FIG. 24.

Refer now to FIGS. 9 and 10, there being shown a fourth preferred embodiment of a vaginal discharge collector, generally designated by reference numeral 40, according to the present invention. In FIG. 9, a top view of the collector 40 is shown. The collector 40 includes a resilient circular rim 41. The body 44 of the collector 40 is a cup-shaped membrane wall extending downward from the rim to form a collection space 49. The membrane wall includes at its bottom a reservoir 42 that is a bubble-like protrusion on the body 44 surface defined by the membrane. As shown in FIGS. 9 and 10, the collector 40 is in a rolled-down position. Like collector 10, as shown in FIGS. 3 and 4, the collector 40 may be positioned in a rolled-up position with the body membrane 44 rolled around the rim 41. In the rolled-up position the space 49 has a smaller volume than it has in the rolled-down position. The collector 40 includes a removal means in the form of a tab 48 which is attached to the rim 41. The tab 48 may be attached to or formed integrally with the rim 41 and has sufficient length to be grasped by the user for removal of the collector 40 from its use position in the vaginal canal. The structure of the rim 41 of the collector 40 includes a telescoping metal core as discussed in greater detail with reference to FIG. 25. The collector 40 has ventilating holes 43 extending through the body 44 near the rim 41. The holes 43 allow air to pass through the body 44 for equalizing pressure in the vaginal canal during insertion and removal of the collector 40. The collector 40 also includes a number of vertically extending ribs 47 which are thickened portions of the inner and outer surface of body 44. The ribs 47 strengthen the body 44.

Refer now to FIGS. 11 and 12, there being shown a fifth preferred embodiment of a vaginal discharge collector, generally designated by reference numeral 50, according to the present invention. In FIG. 11, a top view of the collector 50 is shown. The collector 50 includes a resilient circular rim 51. The body 54 of the collector 50 is a cup-shaped membrane wall extending downward from the rim to form a collection space 59. The membrane wall includes at its bottom a reservoir 52 that is a bubble-like protrusion on the body 54 surface defined by the membrane. As shown in FIGS. 11 and 12, the collector 50 is in a rolled-down position. However, like collector 10 as shown in FIGS. 3 and 4, the collector 50 may be positioned in a rolled-up position with the body membrane 54 rolled around the rim 51. In the rolled-up position the space 59 has a smaller volume than it has in the rolled-down position. The collector 50 includes a removal means in the form of a string 58 which is attached to the rim 51. The string 58 has sufficient length to be grasped by the user for removal of the collector 50 from its use position in the vaginal canal. The structure of the rim 51 of the collector 50 includes an internal wire core as discussed in greater detail with reference to FIG. 26. The collector 50 has ventilating holes 53 extending through the body 54 near the rim 51. The holes 53 allow air to pass through the body 54 for equalizing pressure in the vaginal canal during insertion and removal of the collector 50. The collector 50 also includes a number of horizontally extending ribs 57 which are thickened portions of the inner and outer surface of body 54. The ribs 57 strengthen the body 54.

Refer now to FIG. 13, there being shown a sixth preferred embodiment of a vaginal discharge collector, generally designated by reference numeral 60, according to the present invention. The collector 60 includes a resilient circular rim 61. The body 64 of the collector 60 is a cup-shaped membrane wall extending downward from the rim to form a collection space 69. The membrane wall includes at its bottom a reservoir 62 that is a bubble-like protrusion on the body 64 surface defined by the membrane. Positioned within the collection space 69 of the body 64 is an absorbent pad 65 composed of cotton fiber or other absorbent material. The pad 65 absorbs fluid that enters the collection space 69. The pad 65 may expand upon absorbing fluid to increase its capacity, and the volume of the collector space 69 may be enlarged by any resulting outward deformation of the elastomeric body 64. As shown in FIG. 13, the location of the top surface of the pad 65 is shown in phantom by line 66a with the pad 65 in an initial relatively low absorption state. In this state the pad 65 could be dry or could have absorbed some fluid without expanding substantially, depending upon the properties of the absorbent material of the pad 65. Alternatively, the pad could be sized for the initial upper surface to be located above or below the line 66a of FIG. 13. The line 66b shows the level of the top of the pad 65 at an absorption state relatively higher than the state defined by line 66a and pad 65 has expanded somewhat. The pad 65 does not completely fill the collection space 69 and will inhibit any fluid in the reservoir 62 below the pad 65 from exiting the collector 10. Although the embodiment of FIG. 13 does not include a closure membrane structure, the pad 65 could also be used with a collector having such a closure membrane structure as described herein with respect to various embodiments of the invention. As shown in FIG. 13, the collector 60 is in a rolled-down position. However, like collector 10 as shown in FIGS. 3 and 4, the collector 60 may be positioned in a rolled-up position with the body membrane 64 rolled around the rim 61. In the rolled-up position the space 69 has a smaller volume than it has in the rolled-down position. If necessary, the pad 65 may be removed, such as to adjust the volume of the space 69. The collector 60 includes an apron 67 attached to and extending downward from the rim 61 along the entire periphery of the rim 61. The apron 67 functions to stiffen the rim 61 and to aid in blocking against the passage of matter between the rim 61 and the wall of the vaginal canal and may be useful for delivering substances such as spermicide or medication. The rim 61 includes an inner core 63 encased in the outer elastomeric material of the rim 61 along the entire circumference of the rim 61. The inner core 63 is composed of a plastic material to give the rim 61 increased rigidity. Alternative materials for the core 63 include dense sponge or foam and other polymers. The tab 68 is attached to and may be integrally formed with the reservoir 62 of the body 64. The tab 68 may be grasped for removal of the collector 60 from the vaginal canal.

Refer now to FIGS. 14 and 15, there being shown a seventh preferred embodiment of a vaginal discharge collector, generally designated by reference numeral 70, according to the present invention. In FIG. 14, a top view of the collector 70 is shown. The collector 70 includes a resilient circular rim 71. The body 74 of the collector 70 is a cup-shaped membrane wall extending downward from the rim to form a collection space 79. The membrane wall includes at its bottom a reservoir 72 that is a bubble-like protrusion on the body 74 surface defined by the membrane. As shown in FIGS. 14 and 15, the collector 70 is in a rolled-down position. The collector 70 may be positioned in a rolled-up position with the body membrane 74 rolled around the rim 71. In the rolled-up position the space 79 has a smaller volume than it has in the rolled-down position. The collector 70 includes a closure means in the form of a membrane 73 to inhibit the exit of menses or other vaginal discharge from exiting the collection space 79. The membrane 73 extends around the periphery of the circular area defined by the rim 71 forming with its edge 76 a circular slit 75. The width of the membrane 73 between edges 76 and rim 71 is preferably about five percent to about ninety five percent of the diameter of the rim 71. The collector 70 also includes a number of vertically extending ribs 77 which are thickened portions of the inner and outer surface of body 74. The ribs 77 strengthen the body 70 and extend in a U-shaped manner from the rim 71 vertically downward and back upward to rim 71. The various ribs 77 are positioned substantially parallel to one another.

Refer now to FIG. 16, there being shown an eighth preferred embodiment of a vaginal discharge collector, generally designated by reference numeral 80, according to the present invention. In FIG. 16, a top view of the collector 80 is shown. The collector 80 includes a resilient circular rim 81. Similar to the collector 70 the body 84 of the collector 80 is a cup-shaped membrane wall extending downward from the rim to form a collection space 89. The membrane wall includes at its bottom a reservoir 82 that is a bubble-like protrusion on the body 84 surface defined by the membrane. As shown in FIG. 16, the collector 80 is in a rolled-down position. The collector 80 may be positioned in a rolled-up position with the body membrane 84 rolled around the rim 81. In the rolled-up position the space 89 has a smaller volume than it has in the rolled-down position. The collector 80 includes a closure means in the form of two membranes 83 to inhibit the exit of menses or other vaginal discharge from exiting the collection space 89. The membranes 83 extend across the circular area defined by the rim 83 forming between their edges 86 a slit 85 which extends across the diameter of the rim 81. The edges 86 are straight and substantially parallel so that the width of slit 85 is substantially constant and preferably between about five percent and about ninety five percent of the diameter of rim 81. A curvilinear rib 87 extends along and strengthens each of the membranes 83.

Refer now to FIG. 17, there being shown a ninth preferred embodiment of a vaginal discharge collector, generally designated by reference numeral 90, according to the present invention. The collector 90 includes a resilient circular rim 91. Similar to the collector 70, the body 94 of the collector 90 is a cup-shaped membrane wall extending downward from the rim to form a collection space 99. The membrane wall includes at its bottom a reservoir 92 that is a bubble-like protrusion on the body 94 surface defined by the membrane.

As shown in FIG. 17, the collector 90 is in a rolled-down position. The collector 90 may be positioned in a rolled-up position with the body membrane 94 rolled around the rim 91. In the rolled-up position the space 99 has a smaller volume than it has in the rolled-down position. The collector 90 includes a closure means in the form of a membrane 93 to inhibit the exit of menses or other vaginal discharge from exiting the collection space 99. The membrane 93 extends around the periphery of the circular area defined by the rim 91 forming with its edges 96 a rectangular slit 95. A number of parallel ribs 97 are formed on and strengthen the membrane 93. The area of slit 95 is preferably between about five percent and about ninety five percent of the area defined by rim 91. Alternatively, the slit could be diamond shaped, or have other shapes as desired.

Refer now to FIGS. 19 through 23 which show additional preferred embodiments of the present invention. Each of these embodiments is constructed similar to the collector 10 and as discussed below. FIG. 19 shows a tenth preferred embodiment, a collector 100, having a body 104 and two reservoirs 105 which function similar to reservoir 12 of collector 10. The edges 108 of the two reservoirs 105 meet at ridge 109. In FIG. 20, the eleventh preferred embodiment, collector 110, includes a body 114 having a number of pleated sections 117 of decreasing size to form an inverted cylindrical pyramid shape. FIG. 21 shows the twelfth preferred embodiment, collector 120, which has a cone-shaped body 124 with a rounded point 127. The rim 121 of collector 120 is formed hollow with numerous pleats 122 which extend around the entire rim 121. The pleats 122 allow the rim 121 to be compressed and collapsed to a smaller diameter for insertion of the collector 120 into the vaginal canal. Alternatively, the pleats could extend over only a portion of the rim 121. The thirteenth preferred embodiment of FIG. 22, collector 130, is similar to collector 120 but has a body 134 ending in a relatively sharp point 137. In FIG. 23, the fourteenth preferred embodiment, collector 140, has a body 144 that includes an upper generally cylindrical portion 145 extending from the rim 141 and a lower conical portion 146 extending from the portion 145 at the edge 148 to a lower point 147. Each of the embodiments of FIGS. 20 through 23 have lower extents that tend to form a reservoir space when the collector is in the rolled-up position which reservoir space functions similarly to the reservoir 12 of collector 10.

Figure 26:
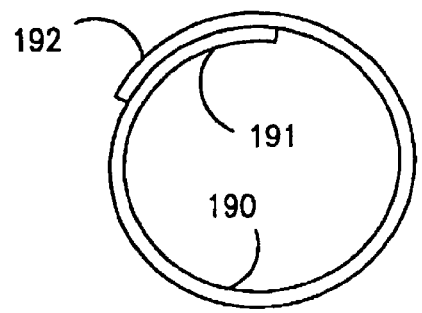
FIG. 26 is a schematic view of the rim structure of the collector of FIG. 11.
Figure 25:
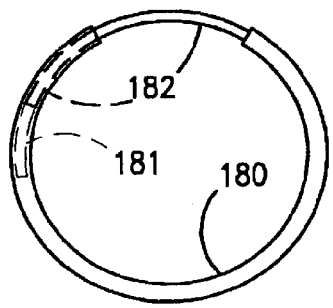
FIG. 25 is a schematic view of the rim structure of the collector of FIG. 9.

Refer now to FIGS. 24 through 26 which show schematically three types of internal rim structures. In each type of structure elastomeric rim material is formed around and seals in the structure. In FIG. 24 a coil spring 170 having a number of small closely turned coils 171 is formed into a circle. A circular inner core 172 extends within the coils 171. The coils 171 are preferably tightly spaced and wrapped around the core 172. The spring materials and the diameters of the wire, the core 172 and the coils 171 are chosen to provide the desired resiliency and spring force for the collector 30. In FIG. 25, a ring 180 has a hollow large end 181 and a thin small end 182 that telescopes inside the end 181. The ring 180 can be compressed with the small end pushed into the large end 182 to make the collector 40 smaller for insertion into the vaginal canal. After insertion, the ring 180 resiliently expands withdrawing the end 182 from the end 181 to some extent to exert outward holding pressure on the vaginal wall. The elastomeric rim 21 is formed so that it is relaxed or slightly stretched with the end 182 fully inserted into the end 181. FIG. 26 shows a ring shaped wire 190 that has overlapping free ends 191 and 192. The ring may be compressed within the hollow rim 51 to decrease the size of the rim 51 during insertion into the vaginal canal.

Figure 27:
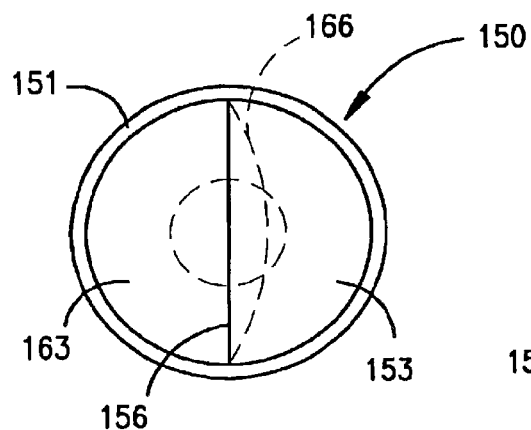
FIG. 27 is a top view of a fifteenth preferred embodiment of a vaginal discharge collector according to the present invention.
Figure 28:
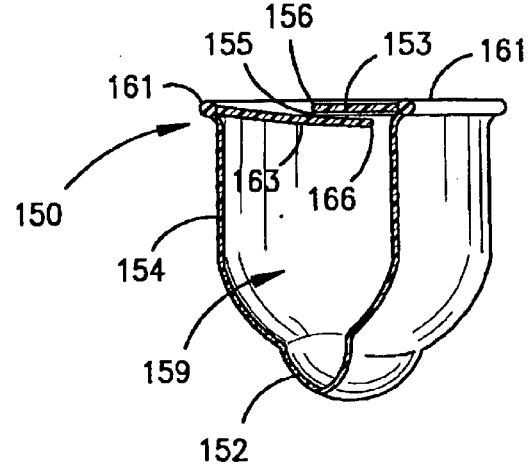
FIG. 28 is a partial cut-away side view of the collector of FIG. 27.

Refer now to FIGS. 27 and 28, there being shown a fifteenth preferred embodiment of a vaginal discharge collector, generally designated by reference numeral 150, according to the present invention. In FIG. 27, a top view of the collector 150 is shown. The collector 150 includes a resilient circular rim 151. The body 154 of the collector 150 is a cup-shaped membrane wall extending downward from the rim to form a collection space 159. The membrane wall includes at its bottom a reservoir 152 that is a bubble-like protrusion on the body 154 surface defined by the membrane. As shown in FIGS. 27 and 28, the collector 150 is in a rolled-down position. However, like collector 10, as shown in FIGS. 3 and 4, the collector 150 may be positioned in a rolled-up position with the body membrane 154 rolled around the rim 151. In the rolled-up position the space 159 has a smaller volume than it has in the rolled-down position.

In order to facilitate the rolling down (or rolling up) operation, the body means 154 and reservoir means 152 are pushed through the slit 155 formed between the edge 156 of the membrane 153 and the edge 166 of the membrane 163. Then, the rim 21 is twisted so that the inner annular surface becomes the outer annular surface (which causes the body means 154 to either roll up or roll down along the circumference of the rim, dependent upon the direction of the twisting motion). The membranes 153 and 163 are each then stretched back over the adjoining portion of rim 21 and allowed to snap back into position on the opposite side of the rim from their starting position. The rim may stay in such position or may continue to twist such that the initial inner annular surface again becomes the inner annular surface, depending upon the elastic properties of the rim and of the components of the collector attached to the rim as well as upon other forces acting on the rim. This results in the collector being turned inside out and the point of attachment of the body to the rim being positioned on the top-facing portion rather than the bottom-facing portion of the rim. In addition, by choosing the membrane material with the appropriate elastic properties, the rim can be rolled to a number of intermediate positions in which the membrane is rolled up in the body wound around the rim.

Note that the body 154 is deeper, preferably about three to about four inches (about eight to about ten centimeters) in depth, and has a larger capacity, preferably about two to four ounces (about thirty to sixty milliliters), than the collector 10 of FIGS. 1 through 4. This embodiment is particularly useful for over-night use or when relatively large volumes of discharge are to be collected. The collector 150 includes a closure means that includes two membranes 153 and 163. The upper membrane 153 extends over approximately half of the area defined by the rim 151 and has no or relatively little slack so that it extends approximately horizontally. The lower membrane 163 extends over more than half of the area defined by the rim 151. The edge 166 of the membrane 163 extends underneath the upper membrane 153. The slit 155 formed between the edge 156 of the membrane 153 and the edge 166 of the membrane 163 allows discharge to drain into the collection space 159. However, as collected fluid moves upward towards exiting the device, force is exerted upward on the membrane 163 to cause it to contact the underside of membrane 153. In this manner, the closure means shuts the slit 155 to inhibit the exit of fluid from the collection space 159.

The rim 151 includes a wire ring 161 encased in the elastomeric rim material. The wire ring 161 is composed of a material known as a shape memory alloy. These alloys resist plastic deformation and may be bent severely and will still return to their original shape. This property is referred to as superelasticity or pseudoelasticity. Some shape memory alloys known as thermoelastic alloys, exhibit superelasticity upon being heated to a certain temperature. One known type of such alloy is composed of about fifty percent titanium, about forty-nine percent nickel and about one percent vanadium. Such alloys are available from Raychem Corporation of Menlo Park, Calif. Other types of shape memory materials may also be used for the rim construction, whether as cores or other interior or exterior components of the rim or as the material for the entire rim, depending upon the appropriateness of the material properties considering design and regulatory requirements.

All of the collectors illustrated in FIGS. 1 through 28 may be formed of the same latex rubber material. However, the materials and the size and thickness of the various components of the invention should be chosen for the considerations discussed with respect to one or more of the preferred embodiments. These conditions may be applicable to each of the preferred embodiments described above, as well as other embodiments of the present invention, even though not individually stated for each embodiment in conjunction with its description above. Although the roll-down and roll-up feature has been described above with respect to a number of embodiments, collectors similar to the described embodiments and other embodiments may be constructed which do not include this feature. Also, various features of the illustrated collectors may be used with other collectors. For example, the gripping means 48 of FIGS. 9 and 10 may be used with any one of the other illustrated collectors. The present invention is not limited to the embodiments illustrated and described in detail herein.

With respect to use of the collector for the delivery of drugs and other substances, the substances may be applied to the collector in a number of ways. The substance, which may be a therapeutic agent, may be applied to the collector by mixing the substance or its precursors with the material of the collector's body, rim, reservoir, membrane, and/or other portion during manufacturing, such as prior to forming the collector during a molding operation by mixing the substance with the ingredients, whether dry or liquid, to be molded. Another way to apply the substance is to inject, impregnate, or absorb it partially or completely through the material (or cavities or porous portions thereof) of the collector's body, rim, reservoir, and/or other portions after such portions have been formed. Yet another way to apply the substance is to coat portions of the collector surface with the substance. Yet another way to apply the substance is to impregnate a pad (such as pad 65) with the substance.

Figure 29:
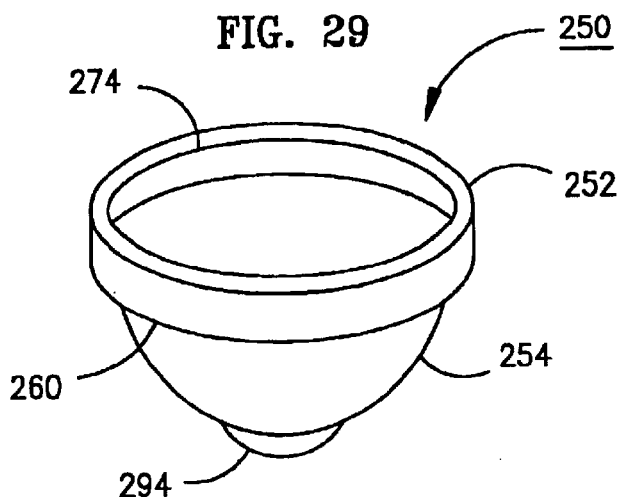
FIG. 29 is a perspective view of a vaginal discharge collection device according to another preferred embodiment of the present invention.
Figure 30:
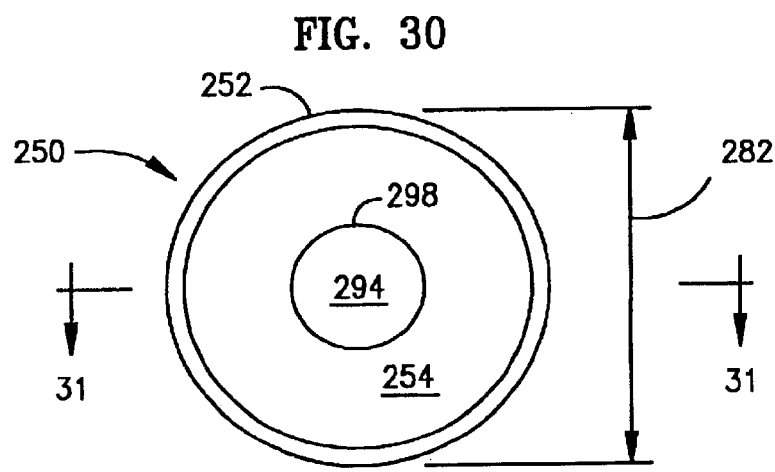
FIG. 30 is a top view of the vaginal discharge collection device of FIG. 29.
Figure 31:
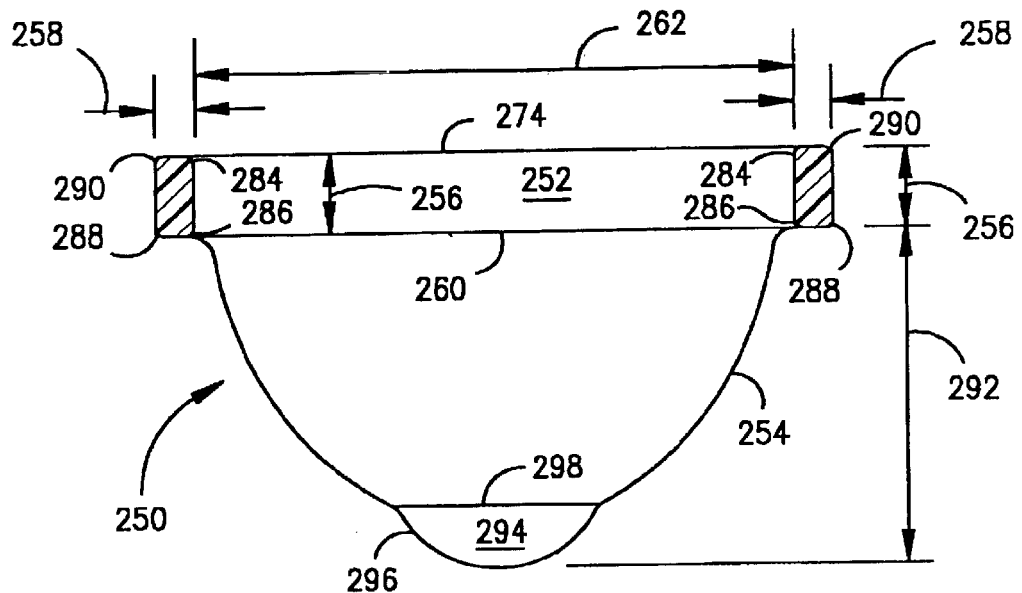
FIG. 31 is a cross sectional view taken along the line 31—31 of FIG. 30.

Refer now to FIGS. 29 and 30, there being shown a vaginal discharge collection device 250 constructed in accordance with another, presently preferred embodiment of the present invention. The collection device 250 is formed of a thick elastomeric rim 252 and a highly flexible reservoir 254. The reservoir 254 is formed of a thin, impervious, elastomeric film material and is sealingly connected to the rim 252. As illustrated in FIG. 31, the rim 252 has a rectangular cross section (with substantially parallel inner and outer sides, and with rounded edges), with its height 256 being substantially greater than its thickness 258.

The amount of discharge typically generated during a menstrual cycle is two to eight tablespoons (thirty to one hundred twenty milliliters). The exemplary devices 250, 10, 20, etc. illustrated in this application are designed to be worn internally for about four hours. During this four hour time period, a woman typically discharges about one teaspoon (five milliliters) of menstrual fluid, although much larger volumes of liquid may be discharged during heavy flow periods.

Figure 32:
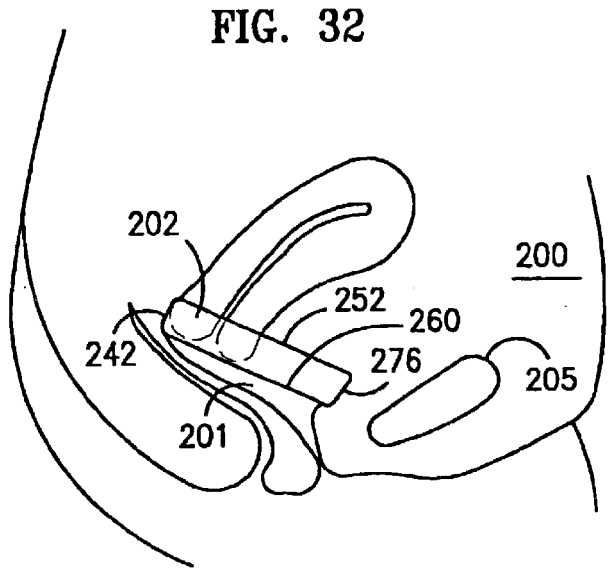
FIG. 32 is a side view of the collection device of FIG. 29 in place within the vaginal canal.

In operation, the device 250 is inserted into the woman's vaginal canal 201 (FIG. 32) such that portions of the rectangular rim 252 are located behind the cervix 202 and behind the pubic bone 205. In this position, the rim 252 is slightly compressed and therefore exerts an elastomeric, radially outwardly directed force on the wall of the vaginal canal 201. This force maintains the device 250 in its illustrated position during use, and prevents vaginal discharge from escaping between the rim 252 and the wall of the vaginal canal 201.

The reservoir 254 can be extended to assume a cup-shaped configuration, as illustrated in FIGS. 29 and 31. However, when the device 250 is in its collection position within the vaginal canal 201 (FIG. 32), the reservoir 254 is collapsed inwardly toward the cervix 202 by the walls of the vaginal canal 201. In this position, i.e., while discharge from the cervix 202 is being collected within the device 250, the reservoir 254 remains in its collapsed configuration essentially coplanar with the bottom edge 260 of the rim 252. Thus, in FIG. 32, the reservoir 254 is essentially hidden from view behind the rim's bottom edge 260.

Vaginal discharge is collected within a generally cylindrical space defined within the rim 252. This collection space is a virtual space in the sense that the rim 252 separates the walls of the vagina 201 to create a collection space where there is no space otherwise. In the illustrated embodiment of the invention, the inner diameter 262 of the rim 252 is approximately sixty two millimeters, and the collection volume is approximately thirty milliliters. The volume of this collection space is approximately equal to the height 256 of the rim 252 times the area surrounded by the rim 252. The reservoir 254 does not contribute significantly to the volume of the collection space, except that folds within the reservoir 254 may provide a trickling down effect, as explained below. While the device 250 is collecting vaginal discharge, the primary function of the reservoir 254 is only to seal off the bottom of the device 250. The ability of the reservoir 254 to assume a collapsed configuration allows the device 250 to be inserted and worn internally with greater comfort.

Figure 33:
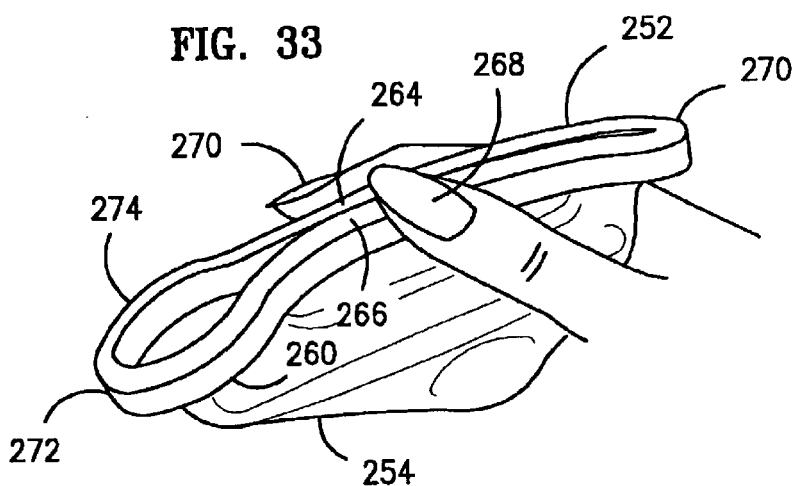
FIGS. 33, 34 and 35 are a perspective view, a top view and a side view, respectively, of the vaginal discharge collection device of FIG. 29, in a compressed configuration ready for insertion.
Figure 34:
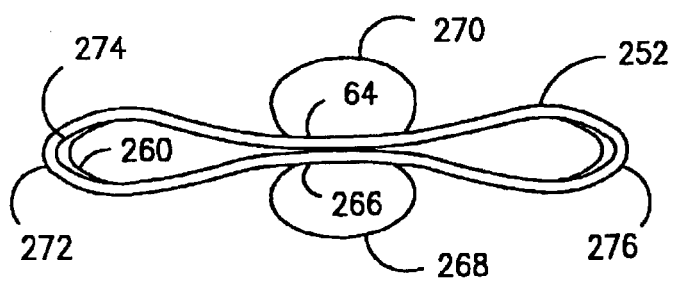

To insert the device 250 into the vaginal canal 201 adjacent the cervix 202, diametrically opposed portions 264, 266 (FIGS. 33 and 34) of the rim 252 are pressed into contact with each other between two of the user's fingers 268, 270 (which may, for example, be the user's thumb 268 and middle finger 270), such that the rim 252 assumes a figure-eight-shaped configuration. The compression applied by the fingers 268, 270 is not released (i.e., the portions 264, 266 remain in contact with each other) until a leading portion 272 of the rim 252 is in position behind the cervix 202. The compression applied by the fingers 268, 270 is then released, allowing the rim 252 to elastomerically restore itself to its initial, generally circular configuration, such that the rim 252 applies a gentle, elastomeric, radially outwardly directed force against the wall of the vaginal canal 201.

Naturally, the opposed portions 264, 266 and the leading and trailing portions 272, 276 of the rim 252 are randomly determined by the user. These portions are not defined until the user grasps the device 250 for insertion. All that is important in this regard is that the portions 264, 266 that come into contact with each other are initially approximately diametrically opposed to each other. The leading and trailing portions 272, 276 will then be defined on opposite sides of the user's fingers 268, 270.

The rectangular cross section of the rim 252 (FIG. 31) is very important. If the thick rim 252 had a circular cross section, it would tend to twist when compressed into the figure-eight-shaped insertion configuration, and further twisting could occur during insertion of the device 250 into the vaginal canal 201. Providing the rim 252 with a generally rectangular cross section therefore is very advantageous in terms of reliability and ease of insertion. Significantly, with the rectangular cross section, the device 250 can be inserted without the insertion tools that are needed with many contraceptive diaphragms.

Figure 35:
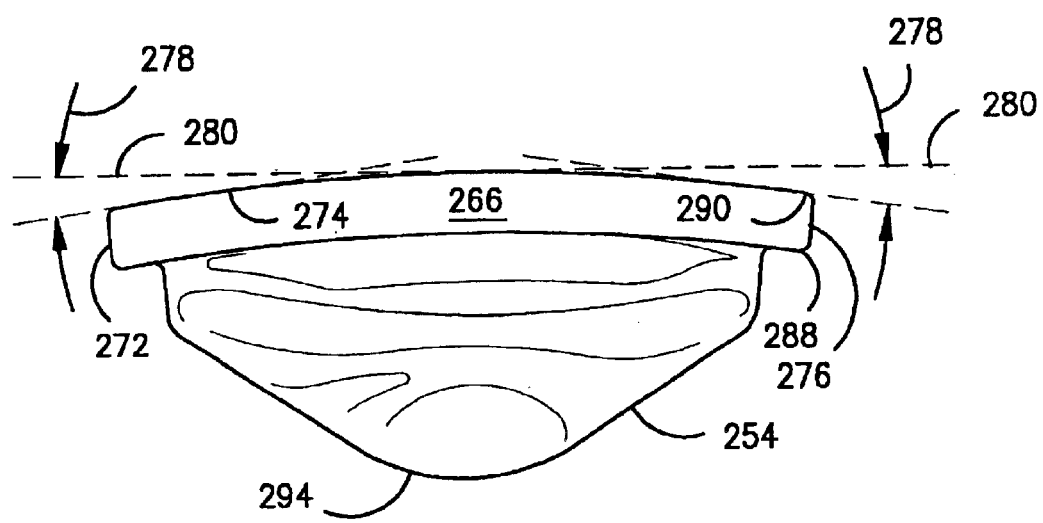

Further, the rim 252 and the reservoir 254 can be arranged such that compressing the rim 252 into its figure-eight-shaped configuration (FIGS. 33, 34 and 35) causes the top edge 274 of the rim 252 to curve slightly downwardly, as illustrated in FIG. 35. The resulting down-dip curvature 278 of the rim's leading portion 272 makes it easier to maneuver the leading portion 272 under the cervix 202 during insertion of the device 250 into the vaginal canal 201. Preferably, the down-dip curvature 278 (i.e., the angular extent to which the leading portion 272 dips downwardly relative to a nominal plane 280 when the rim 252 is in its fully compressed, figure-eight-shaped configuration) is no less than approximately five degrees and no more than approximately fifteen degrees. If the down-dip curvature 278 is too small, some users may have difficulty moving the leading portion 272 underneath the cervix 202 during insertion. If the down-dip curvature 278 is too great, it may be difficult to move the device 250 through the vaginal canal 201.

To remove the device 250, the user inserts her finger into the vaginal canal 201 and grasps a radially inner surface of the rim 252. Preferably, the device 250 is not removed by pulling on the reservoir 254. Since the reservoir 254 is highly flexible, the user's finger can be easily pushed through the plane containing the bottom edge 260 of the rim 252, allowing the user to easily grasp the rim 252. The depth 292 of the reservoir 254 is a significant factor in the removability of the device 250. Increasing the depth 292 makes it easier for the user to insert her finger into proper position for removal of the device 250, i.e., adjacent the inner surface of the rim 252. The device 250 may also be removed by placing the finger over the top edge 274 of the rim 252 and using the finger and the thumb to grasp the rim 252 for removal.

As the device 250 is removed from the vaginal canal 201, the reservoir 254 is automatically extended to its generally cup-shaped configuration (FIG. 31) by the weight of the collected fluid. The ability of the reservoir 254 to extend in this manner minimizes the risk of spilling menstrual fluid discharge during removal and disposal of the device 250. The depth 292 of the extended reservoir 254, as measured from the bottom edge 260 of the rim 252 should be at least approximately thirty millimeters. If the depth 292 were less than approximately thirty millimeters, there may be significant spillage during removal of the device 250 from the vaginal canal 201. Also, if the depth 292 were less than thirty millimeters, some users would find it difficult to grasp the rim 252 to remove the device 250. When the depth 292 is greater than approximately thirty millimeters, the danger of spillage is substantially avoided. A depth 292 greater than approximately fifty millimeters would waste material. Excellent results are obtained when the depth 292 of the film reservoir 254 is approximately forty millimeters. Further, the device 250 may be provided in different sizes, with different depths 292. For example, the depth 292 may be thirty millimeters for a light flow product, forty millimeters for a medium flow product, and fifty millimeters for a heavy flow product.

Further, an increased depth 292 (i.e. a depth 292 greater than thirty millimeters) may provide increased volume for discharge collection through a trickling down effect. In use, the reservoir 254 is collapsed and substantially aligned with the bottom edge 260 of the rim 252. However, there may be folds within the collapsed reservoir 254 that extend downwardly beneath the edge 260, and some discharge may trickle down into such folds. Increasing the depth 292 contributes to this trickle down effect by increasing the number and length of such folds.

The device 250 has an uncomplicated construction so that it can be inexpensively mass produced and marketed. Therefore, once the device 250 has been removed from the vaginal canal 201, it can be simply thrown away and replaced by a new device 250.

The rim 252 is preferably formed of an inert thermoplastic rubber, preferably a blend of two parts of a styrenic-olefinic block copolymer marketed by Shell Chemical Company under the trademark Kraton® and one part low density polyethylene. This blended material is preferred because it is toxicologically acceptable for internal wear, readily available and economical, and readily processible. The block copolymer is particularly preferred because it has anisotropic flow properties, which means that its molecular chains can be caused to orient during plastic flow to increase stiffness perpendicular to the direction of injection molding. Without the anisotropic flow properties of the preferred material, it would be difficult to achieve the desired stiffness perpendicular to the injection molding direction. The low density polyethylene is advantageous because it increases the stiffness of the blend, improves processibility, and reduces the overall cost of the blended material.

The material of the rim 252 should be stiff enough to maintain its shape and provide the desired elastomeric self-restoring force and yet flexible enough to comfortably adjust to individual shapes. The preferred balance between stiffness and flexibility for the material of the rim 252 is obtained when the material has a Shore A hardness of approximately fifty five to approximately seventy five, preferably sixty to seventy, according to the following test method: ASTM D2240. Another important property of the preferred elastomeric material is its ability to relax and conform to the walls of the vagina as its temperature is increased from room temperature to body temperature.

The self-restoring force of the elastomeric rim 252 must be great enough to ensure that the rim 252 will expand with enough strength to form the desired seal against the wall of the vaginal canal 201, and to ensure that the device 250 will not become inadvertently dislodged. On the other hand, the self-restoring force should not be so great as to make it difficult to insert the device 250. A large self-restoring force would also make it difficult to remove the device 250. Moreover, the self-restoring force should be not be so large as to contribute to cramping or cause other discomforts. The preferred material for the rim 252 exhibits a softening effect upon exposure to the temperatures encountered in the vaginal canal 201. This advantageous property allows the rim 252 to more fully conform to the distinct shape of an individual vaginal vault once inserted. This offers greater comfort during wear as well as added protection against potential leakage during use.

Thus, the rim 252 is designed to be relatively stiff at room temperature so as to be easy to insert. The stiffness of the rim 252 decreases after insertion, as its temperature increases, making the device 250 more comfortable to wear and also easier to remove.

The rim 252 has been found to perform well in terms of self-restoring force when the rim 252 has a "compressed hoop strength" of no less than approximately two hundred and fifty grams and no more than approximately seven hundred grams, preferably no less than approximately three hundred and fifty grams and no more than approximately four hundred and fifty grams. Remarkably advantageous results are achieved when the rim's compressed hoop strength is approximately four hundred grams. As used herein, the term "compressed hoop strength" means the force needed to initially maintain the diametrically opposed portions 264, 266 of the elastomeric rim 252 in contact with each other when the rim 252 is in its figure-eight-shaped insertion configuration illustrated in FIGS. 33 and 34, with the rim 252 being at room temperature (approximately twenty three degrees Celsius).

The height 256 of the rim 252 is another important consideration. The reservoir 254 is collapsed and fulfills substantially no reservoir function while the device 250 is collecting discharge, except to seal off the bottom of the device 250. Therefore, the only way to significantly increase the device's collection volume is to increase the rim height 256. However, the rim 252 must not be too high, or it will cause discomfort. The conflicting goals of increased collection volume and increased comfort are satisfactorily balanced when the height 256 of the rim 252 is no less than approximately five millimeters and no more than about fifteen millimeters. Even better results are obtained when the rim height 256 is no less than approximately nine millimeters and no more than approximately eleven millimeters. Within this range, the rim 252 fits snugly and comfortably behind the pubic bone 205. Excellent results are achieved when the rim height 256 is approximately ten millimeters.

The thickness 258 of the rim 252 relative to the rim's height 256 is another important ergonomic consideration. Determining the most advantageous ratio between the height 256 of the rim's parallel sides to the rim's thickness 258 involves trade-offs between space utilization and the stiffness and self-restoring force of the rim 252. If the height to thickness ratio were too great, the rim 252 would either be too high (and therefore uncomfortable) or too flexible (the elastomeric self-restoring force would be too small) such that the rim 252 would tend to twist during insertion. If the ratio were too small, then the rim 252 would form an inadequately small cylindrical collection space and/or would be too thick and would also tend to twist. The best results are achieved when the rim height 256 divided by the rim thickness 258 is no less than approximately two and no greater than approximately three. The most advantageous height to thickness ratio for the preferred embodiment is two and one-half.

An advantage of the present invention is that the diameter of the device 250 does not have to be tailored to an individual user. In particular, the device 250 does not have to fit as tightly as a contraceptive diaphragm. Therefore, the device 250 can be economically manufactured in a single size and still be acceptable for most woman. A preferred outside diameter 282 for the device 250 is seventy millimeters, but satisfactory results for the single size device are achieved when the diameter 282 is no less than approximately sixty eight millimeters and no more than approximately seventy two millimeters.

It may be advantageous to manufacture the device 250 in three different sizes: (1) a junior size for teenage girls; (2) an intermediate size for nulliparous women (i.e., those who have not had a child) during the child-bearing years; and (3) a larger size for multiparous women (i.e., those who have had children). Such devices would have outer diameters 282 as follows: (1) junior—sixty to sixty five millimeters; (2) nulliparous women—sixty six to seventy four millimeters; and (3) multiparous women—seventy five to eighty millimeters. If a "one size fits all" device is desired, then the outer diameter 282 should be approximately seventy millimeters.

The rim 252 preferably has rounded edges 284, 286, 288, 290. This helps make it easy to insert the device 250 into position for use without scraping delicate tissues. Providing the rounded edges 284, 286, 288, 290 also helps avoid tissue damage during use of the device 250.

The device 250 can be formed by an injection molding process involving the following steps: injection molding the rim 252; attaching a sheet of thermoplastic elastomer to the rim 252; and vacuum thermoforming the film reservoir 254 from the sheet of elastomeric material. The above-described blended material is well suited to this injection molding process because of its anisotropic flow properties. Also, the rim 252, by virtue of its rectangular cross section, is relatively easy to injection mold. In particular, with the rectangular cross section, the rim 252 can be produced with a faster cycle time. This is because the cross section of the rim 252 is such that the injection molded material will rapidly cool and solidify. A rim with the same height 256 but with a circular cross section would take longer to solidify.

The film reservoir 254 is formed generally as thin as practically possible. Making the reservoir 254 very thin makes the device 250 easier to use and more comfortable to wear. However, if the reservoir 254 were less than about one and one-half mils thick, the reservoir 254 could cause discomfort and could be easily punctured. A preferred thickness for the reservoir 254 is about two to about six mils. If the reservoir 254 were more than about fifteen mils thick, it might not properly redeploy (extend to its FIG. 31 position) upon removal of the device 250 from the vaginal canal 201.

Advantageously, the reservoir 254 has a dimple 294. During removal of the device 250, vaginal discharge tends to flow into the dimple 294. In the illustrated embodiment, the dimple 294 will hold about one teaspoon (five milliliters) of discharge (i.e., the amount of fluid typically discharged during a four hour wear cycle). The relatively steep side walls 296 of the dimple 294 cause the discharge to remain within the dimple 294, beneath the upper edge 298 of the dimple 294. The dimple 294 forms a deep, isolated location within the device 250 during removal. The effect is to increase the extent to which discharge remains at the bottom of the device 250 during removal, reducing the likelihood of spillage. The dimple 294 also functions as a visual indicator. That is, the upper edge 298 can be easily recognized as a point of reference by the woman removing the device 250, making it easy for the woman to make a comparative determination of the amount of discharge within the device 250. The dimple 294 may also contribute to the trickling down effect by increasing the number of folds within the reservoir 254 and by increasing the volume formed by such folds.

Vaginal discharge collection devices constructed in accordance with the preferred embodiment illustrated in FIGS. 29–35 have been used experimentally with excellent results.

EXAMPLE 1

A study was conducted to determine the acceptability and effectiveness of the present invention. In this study, more than six thousand vaginal discharge collection devices like the device illustrated in FIGS. 29–35 were used over four hundred menstrual cycles. Fifty seven percent of the women who used the device during this study stated that they would use the device as their primary method of sanitary protection. Moreover, it was observed that user satisfaction with the device increased with repeated use. After use of the device for just one menstrual cycle, fifty three percent of the women indicated that they would use the device as their primary method of sanitary protection. After using the device for a second menstrual cycle, fifty eight percent of the women indicated that they would use the device as their primary method of sanitary protection. After use of the device for a third menstrual cycle, sixty one percent of the women indicated that they would use the device as their primary method of sanitary protection. The devices used for this study were constructed like the device 250 illustrated in FIGS. 29–35. Each of the devices had the dimple 294, and a reservoir depth 292 of approximately forty millimeters, a compressed hoop strength of approximately four hundred grams, a height 256 of approximately ten millimeters, a rim height to thickness ratio of approximately two and one-half, and an outside diameter 282 of approximately seventy millimeters. The thickness of the reservoir 254 was within the range of approximately two mils to about six mils. The devices were formed of the Kraton elastomeric material described above.

EXAMPLE 2

To determine the acceptability and effectiveness of the present invention, a study was conducted in which vaginal discharge collection devices like those described in Example 1, with a compressed hoop strength in a range of from approximately three hundred forty grams to approximately five hundred grams, were worn for two hundred sixty seven menstrual cycles. Devices with a compressed hoop strength less than three hundred forty grams would not insert easily for proper internal placement and could easily dislodge. It was found that devices with a compressed hoop strength greater than five hundred grams could cause difficulty upon insertion and could cause discomfort to the user.

Each of the devices illustrated in FIGS. 1–35 may be used to deliver therapeutic agents, such as drugs, into the vaginal canal 201. The substances to be delivered may be impregnated into the device so as to be slowly released while the device is positioned within the canal. The substance may be impregnated into the device by mixing the substance or its precursors into the material of the device prior to formation of the device. Alternatively, the substance may be injected or absorbed into one or more portions of the device after the device has been formed. The substance may also be coated onto one or more portions of the collection devices.

Substances that can be delivered intravaginally by the present invention include timed-release and bolus released, systemic and topical, medicants for all diseases of the vagina and other reproductive organs and any and all diseases of the entire female anatomy where vaginal delivery can be utilized for both menstruating and non-menstruating females. For example, medication for the treatment of yeast and fungal infections can be delivered intravaginally without interruption even during menstruation. The invention may also be used for the delivery of deodorizing materials for odor prevention, for the delivery of lubrication and for the delivery of steroids, hormones, antibacterial agents, and other pharmacological, chemical, natural and homeopathic agents. The invention may also be used for intravaginal delivery of anaesthetic for local and general surgical procedures and for the delivery of pain relieving medication for intermittent and chronic pain.

Figure 36:
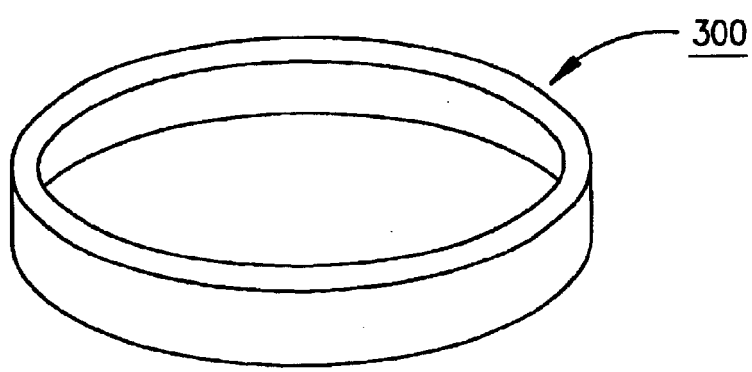
FIG. 36 is a perspective view of an intravaginal drug delivery ring according to the present invention.

The above-described drugs and other substances do not necessarily have to be impregnated or absorbed into or coated on and delivered intravaginally by the devices illustrated in FIGS. 1–35. The drugs and other substances may be delivered intravaginally by the drug delivery ring 300 illustrated in FIG. 36. The ring 300 fits within the vaginal canal 201 just like the rim 252 illustrated in FIG. 31, and the composition and dimensions of the drug delivery ring 300 are identical to those of the rim 252. Therefore, the drug delivery ring 300 has the ergonomic advantages (convenience, comfort and reliability) of the rim 252. Since the ring 300 does not have a reservoir 254, it may be preferable to construct the ring 300 such that it has a compressed hoop strength of up to approximately seven hundred grams.

Moreover, one or more membranes can be provided to augment the utility of the ring 300 as a drug delivery device. For example, a drug-impregnated ring may have a membrane attached to its lower edge, thereby providing for collection of discharge caused by an infection. The attached membrane may itself be filled, coated or impregnated with a substance to be delivered intravaginally. Indeed, such a reservoir membrane may provide extra surface area, which is desirable for certain drug delivery modes. Or, permeable membranes may be stretched over the upper and lower edges of the ring, forming a drum-like structure. When the ring 300 has such a drum-like structure, it may be preferable to construct the device such that it has a compressed hoop strength of down to approximately two hundred fifty grams.

The following examples demonstrate controlled delivery of substances from Kraton® films. The drug-impregnated films of the examples were cast from a solvent and closely approximate the dimensions (thickness, surface area, shape) of the reservoir 254.

EXAMPLE 3

Figure 37:
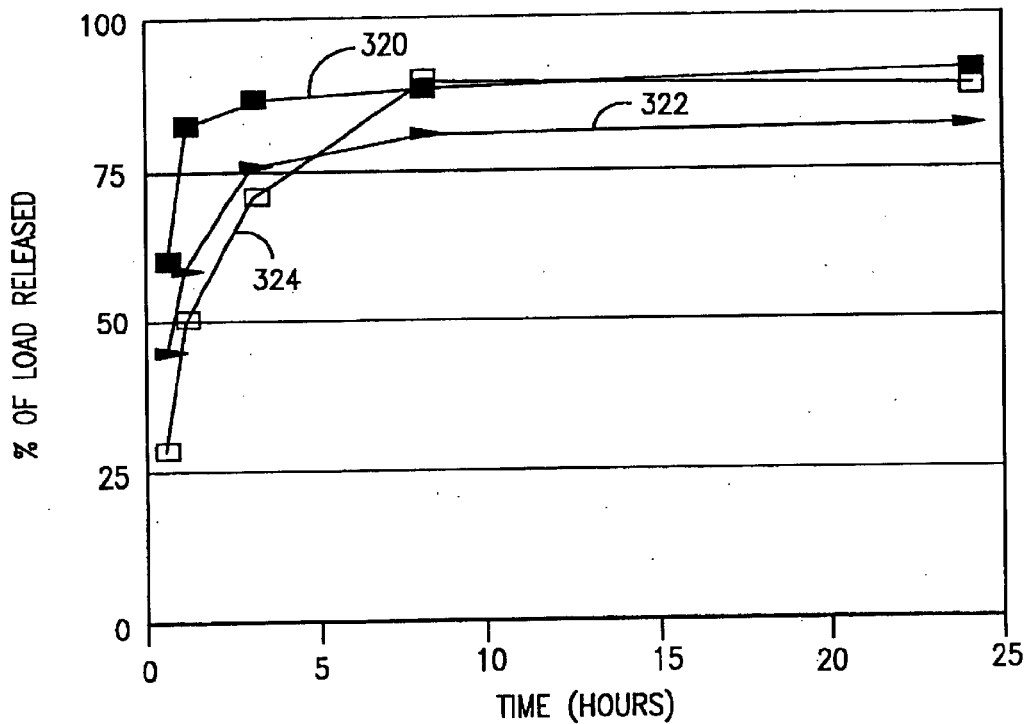
FIG. 37 illustrates the percentage of metronidazole released from Kraton® films containing 0.100, 0.500 and 1.000 gram metronidazole.

A 10% (w/v) solution of Kraton® elastomer in a suitable solvent was prepared. To 10 milliliters of this solution was added either 0.100, 0.500, or 1.000 gram of metronidazole (2-methyl-5-nitroimidazole-1-ethanol), an antiprotozoal used in the treatment of bacterial vaginosis. The mixture was vortexed to produce a homogeneous suspension, and then poured into glass molds. Upon evaporation of the solvent, the resulting films were composed of 1 gram elastomer and either 0.10, 0.50, or 1.00 gram of metronidazole distributed throughout the elastomer. The films were approximately 0.3 millimeter thick and provided a surface area of approximately 65 $cm^2$. The films were placed in a sealed jar containing a volume of simulated vaginal fluid and shaken gently at 37° C. for 24 hours. Samples of the fluid were removed at set time intervals and analyzed quantitatively for metronidazole by high performance liquid chromatography (HPLC). Results of the elutions of the three types of films are shown graphically in FIG. 37, with reference characters 320, 322 and 324 representing the films having 0.10, 0.50 and 1.00 gram of metronidazole distributed therein, respectively.

EXAMPLE 4

Figure 38:
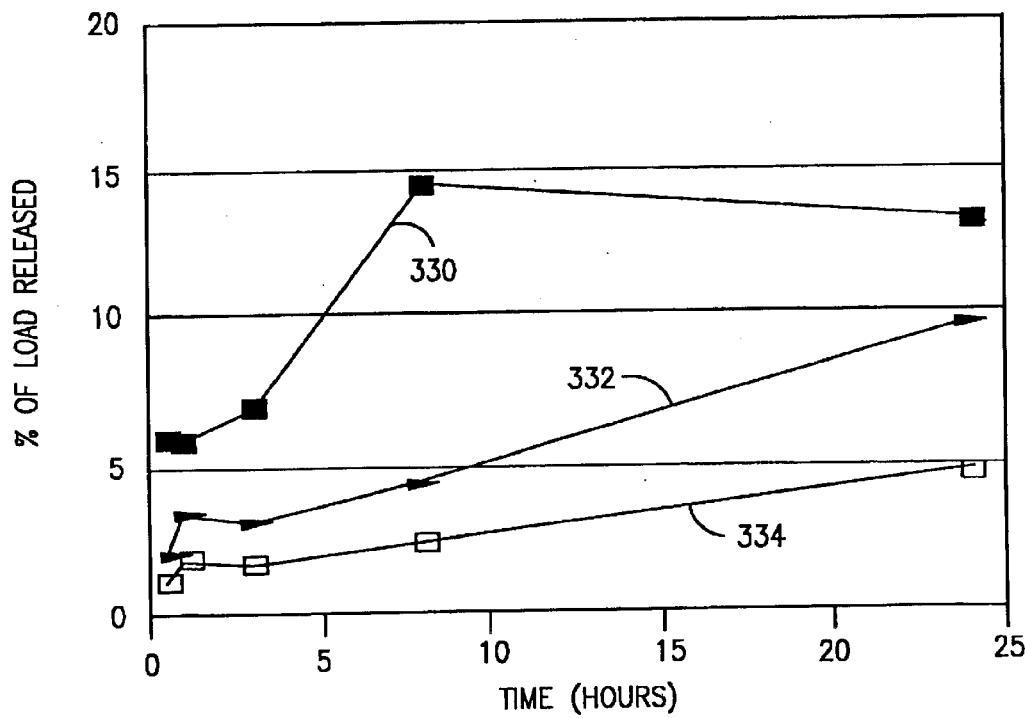
FIG. 38 illustrates the percentage of miconazole nitrate released from Kraton® films containing 0.100, 0.500 and 1.000 gram miconazole nitrate.

A 10% (w/v) solution of Kraton® elastomer in a suitable solvent was prepared. To 10 milliliters of this solution was added either 0.100, 0.500, or 1.000 gram of miconazole nitrate (1-[2-(2,4-dichlorophenyl)-2-[2,4-dicholorophenylmethoxy]ethyl]1H-imidazole nitrate), an antifungal used in the treatment of vaginal candidiasis. The mixture was vortexed to produce a homogeneous suspension, and then poured into glass molds. Upon evaporation of the solvent, the resulting films were composed of 1 gram elastomer and either 0.10, 0.50, or 1.00 gram of miconazole nitrate distributed throughout the elastomer. The films were approximately 0.3 millimeter thick and provided a surface area of approximately 65 cm². The films were placed in a sealed jar containing a volume of simulated vaginal fluid and shaken gently at 37° C. for 24 hours. Samples of the fluid were removed at set time intervals and analyzed quantitatively for miconazole nitrate by high performance liquid chromatography (HPLC). Results of the elutions of the three types of films are shown graphically in FIG. 38, with reference characters 330, 332 and 334 representing the films having 0.10, 0.50 and 1.00 gram of miconazole nitrate distributed therein, respectively.

The invention is not limited to the preferred embodiments described herein. For example, the invention is not restricted to human use. The invention may be used to collect discharge from non-human primates and other animals, and/or for substance delivery for veterinary applications. For non-human primate and other veterinary uses, the dimensions of the devices would be sized or adapted to fit the dimensions of the vaginal canal of the animal concerned.

Moreover, in its broadest aspects, the invention is not limited to the collection of menstrual fluid. The invention may also be used as a specimen collector to collect blood and/or vaginal, cervical and/or uterine discharge, including for diagnostic purposes.

The above description and drawings are only illustrative of preferred embodiments of the present invention, and it is not intended that the present invention be limited thereto. Any modification of the present invention which comes within the spirit and scope of the following claims is to be considered part of the present invention.

What is claimed is:

1. A vaginal discharge collection device, comprising:
an annular elastomeric rim for creating a collection space for collecting vaginal discharge, said rim having a height, said rim having a thickness, and wherein the height of said rim divided by the thickness of said rim is approximately two and one-half; and
a flexible film reservoir attached to said rim.

2. A vaginal discharge collection device, comprising:
an elastomeric rim having a first generally circular configuration for creating a collection space for collecting vaginal discharge, said rim being compressible from said first configuration to a second generally figure-eight-shaped configuration for insertion of said device into position for use, wherein diametrically opposed portions of said rim are in contact with each other when said rim is in said second configuration, and wherein said rim is capable of elastomerically self-restoring itself from said second configuration to said first configuration, and wherein said rim has a height, and wherein said rim has a thickness, and wherein the height of said rim divided by the thickness of said rim is approximately two and one-half; and
a flexible film reservoir attached to said rim.

3. The vaginal discharge collection device of claim 2, wherein said rim is formed of an injection molded thermoplastic rubber.

4. The vaginal discharge collection device of claim 3, wherein said rim has a Shore A hardness of about fifty five to about seventy five.

5. The vaginal discharge collection device of claim 3, wherein said reservoir is collapsible so as to be substantially enclosed within said rim during use.

6. The vaginal discharge collection device of claim 2, wherein said rim has an outer diameter in its first generally circular configuration of no less than approximately sixty one millimeters and no more than approximately eighty millimeters.

7. The vaginal discharge collection device of claim 6, wherein said outer diameter is approximately seventy millimeters.

8. The vaginal discharge collection device of claim 2, wherein said rim has a compression hoop strength of no less than approximately three hundred fifty grams and no more than approximately four hundred fifty grams.

9. The vaginal discharge collection device of claims 8, wherein said compression hoop strength is approximately four hundred grams.

10. The vaginal discharge collection device of claim 2, wherein said reservoir is collapsible so as to be substantially enclosed within said rim during use, and wherein said reservoir is extendable to a cup-shaped configuration.

11. The vaginal discharge collection device of claim 10, with no absorbent material within said reservoir, and wherein said reservoir has a bottom portion, and wherein the distance between said bottom portion of said reservoir and said rim is no less than approximately thirty millimeters when said reservoir is in said cup-shaped configuration.

12. The vaginal discharge collection device of claim 11, wherein the distance between said bottom portion and said rim, when said reservoir is in said cup-shaped configuration, is greater than approximately thirty millimeters and no more than approximately fifty millimeters.

13. The vaginal discharge collection device of claim 12, wherein the distance between said bottom portion and said rim, when said reservoir is in,said cup-shaped configuration, is approximately forty millimeters.

14. The vaginal discharge collection device of claim 2, wherein said rim has rounded edges.

15. A vaginal discharge collection device, comprising:
an elastomeric rim having a first generally circular configuration for creating a collection space for collecting vaginal discharge, said rim being compressible from said first configuration to a second generally figure-eight-shaped configuration for insertion of said device into position for use, wherein diametrically opposed portions of said rim are in contact with each other when said rim is in said second configuration, and wherein said rim is capable of elastomerically self-restoring itself from said second configuration to said first configuration, and wherein said rim has a height, and wherein said rim has a thickness, and wherein the height of said rim divided by the thickness of said rim is approximately two and one-half; and
a flexible film reservoir attached to said rim; and
wherein said rim is formed of an injection molded thermoplastic rubber; and
wherein said rim is formed of approximately two parts styrenic-olefinic block copolymer and approximately one part low density polyethylene.

16. A vaginal discharge collection device, comprising:
an elastomeric rim having a first generally circular configuration for creating a collection space for collecting vaginal discharge, said rim being compressible from said first configuration to a second generally figure-eight-shaped configuration for insertion of said device into position for use, wherein diametrically opposed portions of said rim are in contact with each other when said rim is in said second configuration, and wherein said rim is capable of elastomerically self-restoring itself from said second configuration to said first configuration, and wherein said rim has a height, and wherein said rim has a thickness, and wherein the height of said rim divided by the thickness of said rim is approximately two and one-half; and a flexible film reservoir attached to said rim; and wherein a therapeutic agent is impregnated into said rim.

17. A vaginal discharge collector comprising:

body means for providing a collection space for the collection of discharge and having an annular opening for the passage of discharge into said space, said body means having a top, and said body means including a flexible film;

annular rim means for providing resilient outward holding force sufficient for holding the collector in position during use, said rim means being affixed to said body means proximate the top of said body means, said rim means being concentric with said opening, and wherein said rim means has a height and a thickness, and wherein the height of said rim means is greater than the thickness of said rim means; and wherein said rim means has a top and a bottom, said flexible film being attached to said bottom of said rim means, and wherein said rim means has a generally rectangular cross section and an inner cylindrical surface, said cylindrical surface having a top edge and a bottom edge, said top edge being located at said top of said rim means, said bottom edge being located at said bottom of said rim means, and wherein the distance from said top edge of said cylindrical surface to said bottom edge of said cylindrical surface is greater than the thickness of said rim means; and wherein at least one of said body means and rim means includes a substance released during use of the collector.

18. A collector as in claim 17 wherein said substance is coated onto the surface of at least a portion of said collector.

19. A collector as in claim 17 wherein said substance is injected into at least of a portion of said collector.

20. A collector as in claim 17 wherein said substance is mixed during manufacturing of the collector.

21. A collector as in claim 17 wherein said body means and said rim means are flexible so that said body means may be rolled up on said rim means.

22. A vaginal discharge collection device, comprising:

an elastomeric rim having a first generally circular configuration for creating a collection space for collecting vaginal discharge, said rim being compressible from said first configuration to a second generally figure-eight-shaped configuration for insertion of said device into position for use, wherein diametrically opposed portions of said rim are in contact with each other when said rim is in said second configuration, and wherein said rim is capable of elastomerically self-restoring itself from said second configuration to said first configuration, and wherein said rim has a height, and wherein said rim has a thickness, and wherein the height of said rim divided by the thickness of said rim is approximately two and one-half; and a flexible film reservoir attached to said rim, wherein said flexible film reservoir includes a flexible film; and wherein said rim has a top and a bottom, said flexible film reservoir being attached to said bottom of said rim, and wherein said rim has a generally rectangular cross section and an inner cylindrical surface, said cylindrical surface having an annular top edge and an annular bottom edge, said top edge being located at said top of said rim, said bottom edge being located at said bottom of said rim, and wherein the distance from said top edge of said cylindrical surface to said bottom edge of said cylindrical surface divided by the thickness of said rim is approximately two and one-half, and wherein the diameter of said annular top edge of said cylindrical surface is essentially the same as the diameter of said annular bottom edge of said cylindrical surface.

23. The vaginal discharge collection device of claim 22, wherein the height of said rim is no less than approximately five millimeters and no more than approximately fifteen millimeters.

24. The vaginal discharge collection device of claim 23, wherein the height of said rim is no less than approximately nine millimeters and no more than approximately eleven millimeters.

25. The vaginal discharge collection device of claim 22, wherein said reservoir is in a collapsed condition and is substantially enclosed within said rim.

26. The vaginal discharge collection device of claim 22, wherein said flexible film reservoir is not more than about fifteen mils thick.

* * * * *